US010265384B2

(12) United States Patent
Nissen et al.

(10) Patent No.: US 10,265,384 B2
(45) Date of Patent: Apr. 23, 2019

(54) TABLETS COMPRISING GLP-1 AGONIST AND ENTERIC COATING

(71) Applicant: Novo Nordisk A/S, Bagsvaerd (DK)

(72) Inventors: Birgitte Nissen, Glostrup (DK); Flemming S. Nielsen, Roskilde (DK); Patrick W. Garibay, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/543,620

(22) PCT Filed: Jan. 28, 2016

(86) PCT No.: PCT/EP2016/051795
§ 371 (c)(1),
(2) Date: Jul. 14, 2017

(87) PCT Pub. No.: WO2016/120378
PCT Pub. Date: Aug. 4, 2016

(65) Prior Publication Data
US 2018/0000903 A1  Jan. 4, 2018

(30) Foreign Application Priority Data

| Jan. 29, 2015 | (EP) | ................................. | 15153000 |
| Apr. 7, 2015 | (EP) | ................................. | 15162589 |
| Apr. 7, 2015 | (WO) | ................. | PCT/EP2015/057442 |
| Oct. 7, 2015 | (EP) | ................................. | 15188737 |

(51) Int. Cl.
*A61K 9/28* (2006.01)
*A61K 38/26* (2006.01)
*A61K 9/50* (2006.01)
*A61K 38/17* (2006.01)
*A61K 9/00* (2006.01)
*A61K 35/00* (2006.01)

(52) U.S. Cl.
CPC ............ *A61K 38/26* (2013.01); *A61K 9/0053* (2013.01); *A61K 9/282* (2013.01); *A61K 9/2846* (2013.01); *A61K 9/5026* (2013.01); *A61K 35/00* (2013.01); *A61K 38/1709* (2013.01)

(58) Field of Classification Search
None
See application file for complete search history.

(56) References Cited

U.S. PATENT DOCUMENTS

| 4,525,339 A | 6/1985 | Behl et al. |
| 4,590,062 A | 5/1986 | Jang |
| 4,654,155 A | 3/1987 | Kipp et al. |
| 4,656,161 A | 4/1987 | Herr |
| 4,764,375 A | 8/1988 | Paradissis |
| 4,786,508 A | 11/1988 | Ghebre-Sellassie et al. |
| 4,789,547 A | 12/1988 | Song et al. |
| 4,900,730 A | 2/1990 | Miyauchi |
| 4,996,058 A | 2/1991 | Sinnreich |
| 5,110,606 A | 5/1992 | Geyer et al. |
| 5,169,933 A | 12/1992 | Anderson et al. |
| 5,190,748 A | 3/1993 | Bachynsky et al. |
| 5,221,734 A | 6/1993 | Burk et al. |
| 5,229,103 A | 7/1993 | Eagle et al. |
| 5,229,130 A | 7/1993 | Sharma et al. |
| 5,288,497 A | 2/1994 | Stanley et al. |
| 5,346,701 A | 9/1994 | Heiber et al. |
| 5,393,738 A | 2/1995 | Vonderscher et al. |
| 5,444,041 A | 8/1995 | Owen et al. |
| 5,506,207 A | 4/1996 | Rivier et al. |
| 5,541,155 A | 7/1996 | Leone-Bay et al. |
| 5,626,884 A | 5/1997 | Lockett |
| 5,631,347 A | 5/1997 | Baker et al. |
| 5,633,226 A | 5/1997 | Owen et al. |
| 5,639,469 A | 6/1997 | Benes et al. |
| 5,646,109 A | 7/1997 | Owen et al. |
| 5,650,386 A | 7/1997 | Leone-Bay et al. |
| 5,688,761 A | 11/1997 | Owen et al. |
| 5,707,648 A | 1/1998 | Yiv |
| 5,714,477 A | 2/1998 | Einarsson |
| 5,736,161 A | 4/1998 | Garces et al. |
| 5,807,983 A | 9/1998 | Jiang et al. |
| 5,821,222 A | 10/1998 | Bonse et al. |
| 5,821,230 A | 10/1998 | Jiang et al. |
| 5,840,685 A | 11/1998 | Fujii et al. |
| 5,854,281 A | 12/1998 | Uekama et al. |
| 5,863,555 A | 1/1999 | Heiber et al. |
| 5,912,009 A | 6/1999 | Venkateshwaran et al. |
| 5,952,000 A | 9/1999 | Venkateshwaran et al. |

(Continued)

FOREIGN PATENT DOCUMENTS

| CN | 1243667 A | 2/2000 |
| CN | 101125132 A | 2/2008 |

(Continued)

OTHER PUBLICATIONS

Joshi M et al., Role of Eudragit in Targeted Drug Delivery,International Journal of Current Pharmaceutical Research, 2013, vol. 5, No. 2, pp. 58-62.
Knudsen, Lotte et al "Potent derivatives of glucagon-like peptide-1 with pharmacokinetic properties suitable for once daily administration." Journal of Medicinal Chemistry 2000 vol. 43 No. 9 pp. 1664-1669.
Maher et al., "Safety and efficacy of sodium caprate in promoting oral drug absorption: from in vitro to the clinic," Adv. DruQ Del. Rev. 61:1427-1449 (2009).

(Continued)

*Primary Examiner* — Susan T Tran
(74) *Attorney, Agent, or Firm* — Rosemarie R. Wilk-Orescan

(57) ABSTRACT

The present invention relates to solid pharmaceutical compositions for oral administration comprising a GLP-1 agonist, an absorption enhancer which is a salt of medium-chain fatty acid, and an enteric coating as well as uses thereof.

16 Claims, No Drawings
Specification includes a Sequence Listing.

(56) References Cited

U.S. PATENT DOCUMENTS

| | | | |
|---|---|---|---|
| 5,977,175 A | 11/1999 | Lin | |
| 5,998,432 A | 12/1999 | Walsh et al. | |
| 6,001,390 A | 12/1999 | Yum et al. | |
| 6,004,984 A | 12/1999 | Goulet et al. | |
| 6,015,801 A | 1/2000 | Daifotis et al. | |
| 6,017,559 A | 1/2000 | Mulqueen et al. | |
| 6,017,944 A | 1/2000 | Chu et al. | |
| 6,025,366 A | 2/2000 | Walsh et al. | |
| 6,068,850 A | 5/2000 | Stevenson et al. | |
| 6,077,847 A | 6/2000 | Walsh et al. | |
| 6,077,858 A | 6/2000 | Goulet et al. | |
| 6,124,261 A | 9/2000 | Stevenson et al. | |
| 6,147,088 A | 11/2000 | Goulet et al. | |
| 6,150,352 A | 11/2000 | Goulet et al. | |
| 6,150,522 A | 11/2000 | Goulet et al. | |
| 6,156,767 A | 12/2000 | Goulet et al. | |
| 6,156,772 A | 12/2000 | Goulet et al. | |
| 6,200,602 B1 | 3/2001 | Watts et al. | |
| 6,214,798 B1 | 4/2001 | Semple et al. | |
| 6,235,712 B1 | 5/2001 | Stevenson et al. | |
| 6,248,363 B1 | 6/2001 | Patel et al. | |
| 6,270,804 B1 | 8/2001 | Getz et al. | |
| 6,296,881 B1 | 10/2001 | Hata et al. | |
| 6,326,360 B1 | 12/2001 | Kanazawa et al. | |
| 6,372,728 B1 | 4/2002 | Ungell | |
| 6,379,960 B1 | 4/2002 | Popoff et al. | |
| 6,468,559 B1 | 10/2002 | Chen et al. | |
| 6,524,557 B1 | 2/2003 | Backstrom et al. | |
| 6,638,530 B1 | 10/2003 | Ishibashi et al. | |
| 6,747,014 B2 | 6/2004 | Teng et al. | |
| 6,747,125 B1 | 6/2004 | Hoeger et al. | |
| 6,875,843 B2 | 4/2005 | Jacobson | |
| 6,949,258 B2 | 9/2005 | Zhang | |
| 7,098,305 B2 | 8/2006 | Deghenghi et al. | |
| 7,154,002 B1 | 12/2006 | Bressi et al. | |
| 7,214,662 B2 | 5/2007 | Sarlikiotis et al. | |
| 7,410,957 B2 | 8/2008 | Bauss et al. | |
| 7,605,123 B2 | 10/2009 | Radhakrishnan et al. | |
| 7,658,938 B2 | 2/2010 | Cumming et al. | |
| 7,670,626 B2 | 3/2010 | Clancy et al. | |
| 7,704,977 B2 | 4/2010 | Leonard | |
| 8,053,429 B2 | 11/2011 | Cumming et al. | |
| 8,119,159 B2 | 2/2012 | Cumming et al. | |
| 8,323,689 B2 | 12/2012 | Cumming et al. | |
| 8,323,690 B2 | 12/2012 | Cumming et al. | |
| 8,389,008 B2 * | 3/2013 | Baichwal | A61K 9/286 424/464 |
| 8,795,634 B2 | 8/2014 | Illum et al. | |
| 8,828,431 B2 | 9/2014 | Cumming et al. | |
| 8,999,383 B2 | 4/2015 | Lee et al. | |
| 2002/0002140 A1 | 1/2002 | Holick et al. | |
| 2003/0031757 A1 | 2/2003 | Akashe et al. | |
| 2003/0091637 A1 * | 5/2003 | Petereit | A61K 9/5078 424/482 |
| 2003/0100509 A1 | 5/2003 | Sarlikiotis et al. | |
| 2003/0114525 A1 | 6/2003 | Kammer et al. | |
| 2003/0139378 A1 | 7/2003 | Daifotis et al. | |
| 2003/0166508 A1 | 9/2003 | Zhang | |
| 2003/0176397 A1 | 9/2003 | Lichtenberger | |
| 2003/0181421 A1 | 9/2003 | Horowitz et al. | |
| 2004/0087631 A1 | 5/2004 | Bacopoulos et al. | |
| 2004/0147484 A1 | 7/2004 | Boyd et al. | |
| 2005/0065117 A1 | 3/2005 | Lee | |
| 2005/0080075 A1 | 4/2005 | Nichols et al. | |
| 2005/0119331 A1 | 6/2005 | Butler et al. | |
| 2005/0157799 A1 | 7/2005 | Raman et al. | |
| 2005/0163849 A1 | 7/2005 | Wong et al. | |
| 2005/0221501 A1 | 10/2005 | Arnot et al. | |
| 2005/0232981 A1 | 10/2005 | Ben-Sasson | |
| 2005/0249799 A1 | 11/2005 | Jacob et al. | |
| 2005/0260262 A1 | 11/2005 | Dansereau et al. | |
| 2006/0018874 A1 | 1/2006 | Radhakrishnan et al. | |
| 2006/0135405 A1 | 6/2006 | Rischer et al. | |
| 2006/0210639 A1 | 9/2006 | Liversidge et al. | |
| 2007/0021357 A1 | 1/2007 | Tobia et al. | |
| 2007/0021378 A1 | 1/2007 | Varki et al. | |
| 2007/0060509 A1 | 3/2007 | Kanikanti et al. | |
| 2007/0077313 A1 | 4/2007 | Krebs et al. | |
| 2007/0148228 A1 | 6/2007 | Cumming et al. | |
| 2007/0212395 A1 | 9/2007 | Donello et al. | |
| 2007/0219131 A1 | 9/2007 | Ben-Sasson | |
| 2007/0292512 A1 | 12/2007 | Leonard et al. | |
| 2008/0171848 A1 | 7/2008 | Christiansen et al. | |
| 2008/0213366 A1 | 9/2008 | Gowan, Jr. et al. | |
| 2008/0234200 A1 | 9/2008 | Quay et al. | |
| 2008/0275001 A1 | 11/2008 | Cumming et al. | |
| 2008/0318837 A1 | 12/2008 | Quay et al. | |
| 2009/0004281 A1 | 1/2009 | Nghiem et al. | |
| 2009/0060861 A1 | 3/2009 | Poulsen | |
| 2009/0274758 A1 | 11/2009 | Pinhasi et al. | |
| 2009/0280169 A1 | 11/2009 | Leonard | |
| 2009/0280170 A1 | 11/2009 | Lee et al. | |
| 2010/0022480 A1 | 1/2010 | Leonard | |
| 2010/0028421 A1 | 2/2010 | Cumming et al. | |
| 2010/0105627 A1 | 4/2010 | Salama et al. | |
| 2010/0215743 A1 | 8/2010 | Leonard | |
| 2010/0247640 A1 | 9/2010 | Leonard | |
| 2011/0142889 A1 | 6/2011 | Lee et al. | |
| 2011/0171140 A1 | 7/2011 | Illum et al. | |
| 2011/0182985 A1 | 7/2011 | Coughlan et al. | |
| 2012/0156294 A1 | 6/2012 | Leonard et al. | |
| 2012/0189692 A1 | 7/2012 | Cullen et al. | |
| 2012/0231074 A1 | 9/2012 | Santanach-Delisau et al. | |
| 2013/0089604 A1 | 4/2013 | Cumming et al. | |
| 2013/0195939 A1 | 8/2013 | Kidron | |
| 2013/0345134 A1 * | 12/2013 | Sauerberg | A61K 9/2013 514/11.7 |
| 2015/0072940 A1 * | 3/2015 | Chandy | A61K 38/16 514/21.3 |
| 2018/0000903 A1 | 1/2018 | Nissen et al. | |
| 2018/0263915 A1 | 9/2018 | Nybo et al. | |

FOREIGN PATENT DOCUMENTS

| | | |
|---|---|---|
| EP | 0370481 A2 | 5/1990 |
| EP | 0376534 A1 | 7/1990 |
| EP | 0497162 A1 | 8/1992 |
| EP | 0517211 A1 | 12/1992 |
| EP | 0580074 A1 | 1/1994 |
| EP | 0667148 A1 | 8/1995 |
| EP | 747390 | 12/1996 |
| EP | 1154761 A1 | 11/2001 |
| EP | 1246839 B1 | 6/2004 |
| EP | 1674082 A1 | 6/2006 |
| EP | 1339411 B1 | 7/2007 |
| EP | 1154761 B1 | 2/2008 |
| GB | 953626 A | 3/1964 |
| GB | 2212396 A | 7/1989 |
| GB | 2336311 A | 10/1999 |
| IE | (11) 63119 | 3/1995 |
| JP | S59-073600 A | 4/1984 |
| JP | S62-283930 A | 12/1987 |
| JP | H02-180837 A | 7/1990 |
| JP | H02-282327 A | 11/1990 |
| JP | H03-275633 A | 12/1991 |
| JP | H04-149126 A | 5/1992 |
| JP | H0640949 A | 2/1994 |
| JP | H06-192107 A | 7/1994 |
| JP | H11-035458 A | 2/1999 |
| JP | H11-510506 A | 9/1999 |
| JP | 2002/537321 A | 11/2002 |
| JP | 2004/529953 A | 9/2004 |
| JP | 2006/089496 A | 4/2006 |
| RU | 2068689 C1 | 11/1996 |
| WO | 84/04674 A1 | 12/1984 |
| WO | 93/09785 A1 | 5/1993 |
| WO | 93/21907 A1 | 11/1993 |
| WO | 94/08599 A1 | 4/1994 |
| WO | 94/10983 A1 | 5/1994 |
| WO | 95/22319 A1 | 8/1995 |
| WO | 95/34294 A1 | 12/1995 |
| WO | 97/05903 A2 | 2/1997 |
| WO | 97/44017 A1 | 11/1997 |
| WO | 98/01159 A2 | 1/1998 |

(56) References Cited

FOREIGN PATENT DOCUMENTS

| | | |
|---|---|---|
| WO | 99/01579 A1 | 1/1999 |
| WO | 99/02120 A2 | 1/1999 |
| WO | 99/02485 A1 | 1/1999 |
| WO | 99/18972 A1 | 4/1999 |
| WO | 99/45934 A1 | 9/1999 |
| WO | 00/22909 A2 | 4/2000 |
| WO | 0050012 A1 | 8/2000 |
| WO | 00/61111 A1 | 10/2000 |
| WO | 01/82903 A1 | 11/2001 |
| WO | 01/89479 A2 | 11/2001 |
| WO | 02/20037 A1 | 3/2002 |
| WO | 02/064148 A2 | 8/2002 |
| WO | 02/087597 A1 | 11/2002 |
| WO | 02/092069 A1 | 11/2002 |
| WO | 02/092070 A1 | 11/2002 |
| WO | 03/033999 A2 | 1/2003 |
| WO | 03/016332 A2 | 2/2003 |
| WO | 03/045419 A1 | 6/2003 |
| WO | 03/47493 A2 | 6/2003 |
| WO | 03/051373 A1 | 6/2003 |
| WO | 03/053401 A2 | 7/2003 |
| WO | 03/072123 A1 | 9/2003 |
| WO | 2005016312 A1 | 2/2005 |
| WO | 2005/041928 A1 | 5/2005 |
| WO | 2005/055973 A2 | 6/2005 |
| WO | 2005/063218 A2 | 7/2005 |
| WO | 2005/072747 A1 | 8/2005 |
| WO | 2005/115331 A2 | 12/2005 |
| WO | 2006/010155 A2 | 1/2006 |
| WO | 2006/069641 A1 | 7/2006 |
| WO | 2006/102117 A1 | 9/2006 |
| WO | 2006097537 A2 | 9/2006 |
| WO | 2006/103657 A2 | 10/2006 |
| WO | 2006/116565 A2 | 11/2006 |
| WO | 2007117706 A2 | 10/2007 |
| WO | 2007/124090 A2 | 11/2007 |
| WO | 2009/118722 A2 | 10/2009 |
| WO | 2009/137080 A1 | 11/2009 |
| WO | 2009137078 A1 | 11/2009 |
| WO | 2010020978 A1 | 2/2010 |
| WO | 2010/032140 A2 | 3/2010 |
| WO | 2010/099255 A1 | 9/2010 |
| WO | 2011/084618 A2 | 7/2011 |
| WO | 2011/120033 A1 | 9/2011 |
| WO | 2013148966 A1 | 10/2013 |
| WO | 2014060472 A1 | 4/2014 |
| WO | 2014191545 A1 | 12/2014 |

OTHER PUBLICATIONS

Massa et al., "3-(4-Aroyl-1 H-pyrrol-2-yl)-N-hydroxy-2-propenamides, a New Class of Synthetic Histone Deacetylase Inhibitors," J. Med. Chem. 44:2069-2072 (2001).
Mechanick et al., "Effect of a Convenient Single 90-mg Pamidronate Dose on Biochemical Markers of Bone Metabolism in Patients With Acute Spinal Cord Injury," J. Spinal Cord Med. 29(4):406-412 (2006).
Mishima et al., "Studies on the Promoting Effects of Medium Chain Fatty Acid Salts on the Nasal Absorption of Insulin in Rats," J. Pharmacobio-Dyn. 10:624-631 (1987).
Moradei et al., "Histone deacetylase inhibitors: Latest developments, trends and prospects," Curr. Med. Chem. 5(5):529-560 (2005).
Morishita et al., "Site-Dependent Effect of Aprotinin, Sodium Caprate, Na2EDTA and Sodium Glycocholate on Intestinal Absorption of Insulin," Biol. Pharm. Bull. 16:68-72 (1993).
Motlekar, "Oral delivery of low-molecular-weight heparin using sodium caprate as absorption enhancer reaches therapeutic levels," J. Druq Tan:ietinq 13(10):573-583 (2005).
Murakami et al., "Effect of Oleic Acid Vesicles on Intestinal Absorption of Carboxyfluorescein in Rats", Pharm. Res. 3(1):35-40 (1986).
Muranishi et al Drug Devel Ind Pharm vol. 19 p. 929 1993.

Muranishi, "Absorption Enhancers," Grit. Rev. Ther. Drug Carrier Systems 7:1-33 (1990).
Octreotide, Wikipedia. Printed Mar. 23, 2009. 3 pp.
ODA (Inamori), "Absorption Enhancement of Argatroban by Medium Chain Fatty Acid Sodium Salts," Proceedings Int'l Symp. Control. Rel. Bioact. Mater. 24:283-284 (1997).
Palin et al., "The oral absorption of cefoxitin from oil and emulsion vehicles in rats," Int. J. of Pharmaceutics 33:99-104 (1986).
Poster Presentation entitled "A Phase I Trial and Pharmacokinetic Study of Depsipeptide in Pediatric Patients with Refractory Solid Tumors: A Children's Oncology Group Study" at American Society of Clinical Oncology meeting, May 2005, abstract 8528 (Fouladi et al.).
Sawada et al., "Role of Paracellular Pathway in Nonelectrolyte Permeation Across Rat Colon Epithelium Enhanced by Sodium Caprate and Sodium Caprylate," Pharm. Res. 8(11):1365-1371 (1991).
Sawyer et al., "Body surface area as a determinant of pharmacokinetics and drug dosing," Invest. New Drugs 19:171-177 (2001).
Schneider et al., "Evaluation of drug penetration into human skin ex vivo using branched fatty acids and propylene qlycol," Int. J. Pharm. 145:187-196 (1996).
Schnitzer, T. et al., "Therapeutic equivalence of alendronate 70mg once-weekly and alendronate 10mg daily in the treatment of osteoporosis", Aging Clin. Exp. Res. 12:1-12 (Jan. 2000).
Sikora, "Cancer drug development in the post-genomic age," Curr. Sci. 81:549-54 (2001).
Simpson et al., "Significance of non-esterified fatty acids in iron uptake by intestinal brush-border membrane vesicles," Biochim. Biophys. Acta 941:39-47 (1988).
Sinko, "Martin's Physical Pharmacy and Pharmaceutical Sciences," 5m Ed., Lippincott Williams & Wilkins, 355-357 (2006).
Somatostatin, Wikipedia. Printed Mar. 23, 2009. 4 pp.
Tak et al. "The pathogenesis and prevention of joint damage in rheumatoid arthritis: Advances from synovial biopsy and tissue analysis" Arthritis Rheumatism 2000 vol. 43 Issue 12 pp. 2619-2633.
Tanaka et al. "Enhancement of intestinal transport of thyrotropin-releasing hormone via a carrier-mediated transport system by chemical modification with lauric acid," Biochim. Biophys. Acta 1283:119-126 (1996).
Tomita et al., "Absorption-Enhancing Mechanism of Sodium Caprate and Decanoylcarnitine in Caco-2 Cells," J. Pharmacol. Exp. Ther. 272(2):739-743 (1995).
Tomita et al., "Differences in the Enhancing Effects of Sodium Caprate on Colonic and Jejunal Drug Absorption," Pharm. Res. 9(5):648-653 (1992).
Tomita et al., "Enhancement of Colonic Drug Absorption by the Transcellular Permeation Route," Pharm. Res. 5(12):786-789 (1988).
Tomita et al., "Enhancement of Colonic Drug Absorption by the Paracellular Permeation Route," Pharm. Res. 5(6):341-346 (1988).
Uchida et al., "Availability of lactoferrin as a natural solubilizer of iron for food products," Int. Dairy J. 16:95 (2006).
Uchida et al., "Pharmacological and clinical profile of once weekly alendronate for the treatment of osteoporosis (Fosamac35 mg/Bonalon 35 mg)" Folia Pharmacologica Japonica 130:305-312 (2007).
Vetter et al., "Development and in vivo availability study of an oral fondaparinux delivery system," Eur. J. Pharm. Sci. 41:489-497 (2010).
Wood-Kaczmar et al "Understanding the molecular causes of Parkinson's disease" Trends Mol. Med. 2006 vol. 12 No. 11 pp. 521-528.
WPI Database, Accession No. 1984-142694, English language abstract of JP 59073600.
WPI Database, Accession No. 1992-028863, English language abstract of JP 03275633.
WPI Database, Accession No. 1997-287727, English language abstract of RU 2068689.
Yamamoto et al., "Improvement of intestinal absorption of peptide and protein drugs by chemical modification with fatty acids," Nihon Rinsho 56(3):601-607 (1998).

(56) References Cited

OTHER PUBLICATIONS

Yamamoto et al., "Pulmonary absorption enhancement of peptides by absorption enhancers and protease inhibitors," J. Control. Release 41:57-67 (1996).
Yang et al., Deposition of insulin powders for inhalation in vitro and pharmacodynamic evaluation of absorption promoters in rats, Acta Pharmaceutica Sinica 40:1069-1074 (2005).
Yeh et al., "Effect of Medium-Chain Glycerides on Physiological Properties of Rabbit Intestinal Epithelium in Vitro," Pharm. Res. 11(8):1148-1154 (1994).
Zhou et al., "Effects of cholic acid and other enhancers on the bioavailability of insulin from a subcutaneous site," Int. J. Pharm. 69:29-41 (1991).
Zips et al., "New anticancer agents: in vitro and in vivo evaluation," In vivo 19:108 (2005).
Pharmaceutical Excipients Directory 1996, p. 130, 131, 77, Yakuji Nippo Limited.
Akira Yamamoto et al. "Pulmonary absorption enhancement of peptides by absorption enhancers and protease inhibitors" Journal of Controlled Release 1996 vol. 41 No. 1 pp. 57-67. JP OA.
Leonard et al., "Promoting absorption of drugs in humans using medium-chain fatty acid-based solid dosaQe forms: GIPET," Expert Ooin. DruQ Deilv. 3:685-692 (2006).
Motohiro Mishima et al. "Studies on the Promoting Effects of Medium Chain Fatty Acid Salts on the Nasal Absorption of Insulin in Rats" Journal of Pharmacobio-Dynamics 1987 vol. 10 No. 11 pp. 624-631. JP OA.
Xin Hua Zhou et al. "Effects of cholic acid and other enhancers on the bioavailability of insulin from a subcutaneous site" International Journal of Pharmaceutics 1991 vol. 69 No. 1 pp. 29-41. JP OA.
Kidron et al "A Novel Per-Oral Insulin Formulation: Proof of Concept Study in Non-Diabetic Subjects" Diabetic Medicine 2004 vol. 21 No. 4 pp. 354-357.
Mathot F et al "Intestinal Uptake and biodistribution of novel polymeric micelles after oral administration" Journal of Controlled Release, 2006, vol. 111, No. 1-2, pp. 47-55.
Mathot F et al "Transport mechanisms of mmePEG750P(CL-co-TMC) polymeric micelles across the intestinal barrier" Journal of Controlled Release, 2007, vol. 124, No. 3, pp. 134-143.
Mathot et al "Passive diffusion of polymeric surfactants across lipid bilayers" Journal of Controlled Release, 2007, vol. 120, No. 1-2, pp. 79-87.
"McGraw-Hill Dictionary of Chemical Terms", McGraw-Hill Book Company Ed. S.P. Parker, New York pp. 208, 209, 251 (1985).
130 Anemias Caused by Deficient Erythropoiesis, The Merck Manual, 18 Edition, 2006, p. 1036-1047.
Abrahamson et al "Synthesis and characterization of iron stearate compounds" J Inorg Chem 1994 vol. 54 No. 2 pp. 115-130.
Allen, "Ansel's Pharmaceutical Dosage Forms and Drug Delivery Systems" 8th Edition Lippincott Williams & Wilkins, 51-58 2005.
Anderberg et al "Sodium Caprate Elicits Dilatations in Human Intestinal Tight Junctions and Enhances Drug Absorption by the Paracellular Route" Pharm. Res. 1993 vol. 10 No. 6 pp. 857-864.
Andriuoli et al., "Heparin by Alternative Routes of Administration", Haemostasis 20:(suppl 1):154-158 (1990).
Appendix A: Webpage publication provided by Lambent Technologies www.petroferm.com/prodinfo.asp?bus=2&mkt=4&app=3 (2006).
Artursson, "Epithelial Transport of Drugs in Cell Culture. I: A Model for Studying the Passive Diffusion of Drugs over Intestinal Absorbtive (Caco-2) Cells," J Pharm Studies 79(7):476-482 (1990).
Aungst et al., "Enhancement of the intestinal absorption of peptides and non-peptides," J. Control. Release 41:19-31 (1996).
Aungst, "Structure/effect studies of fatty acid isomers as skin penetration enhancers and skin irritants," Pharm. Res. 6:244-247 (1989).
Baker et al., "Role of Body Surface Area in Dosing of Investigatioanl Agents in Adults, 1991-2001," J. Natl. Cancer Inst. 94:1883-1888 (2002).

Bennett et al., "Pulmonary Delivery of Detirelex by Intratracheal Instillation and Aerosol Inhalation in the Briefly Anesthetized Dog," Pharm. Res. 11:1048-1054 (1994).
Bird "Genetic aspects of Alzheimer Disease" Genet. Med. 2008 vol. 10 Issue 4 pp. 231-239.
Brayden et al., "Heparin Absorption Across the Intestine: Effects of Sodium N-[8-(2-Hydroxybenzoyl)Amino] Caprylate in Rat in Situ Intestinal Instillations and in Caco-2 Monolayers," Pharm. Res. 14(12):1772-1779 (1997).
Breddin "The Role of Antithrombin Agents and Factor Xa-Inhibitors in Antithrombotic Treatment" Turk. J. Haematol. 2002 vol. 19 No. 2 pp. 113-120.
Chan et al., "Depsipeptide (FR901228, NSC-630176) pharmacokinetics in the rat by LC/MS/MS," Invest. New Drugs 15:195-206 (1997).
Choay et al., "Structure-activity relationship in heparin: A synthetic pentasaccharide with high affinity for antithrombin III and eliciting high anti-factor Xa activity," Biochem. Biophys. Res. Commun. 116:492-499 (1983).
Cosman, F. et al., "Clinical Evaluation of Novel Bisphosphonate Dosing Regimens in Osteoporosis: The Role of Comparative Studies and Implications for Future Studies", Clin. Ther. 29: 1116-1127 (Jul. 18, 2007).
Cullen et al., "Oral delivery of fondaparinux: A potential patient benefit in thrombosis therapy," Poster presentation at the 2010 MPS Annual Meeting and Exposition; Nov. 14-18, 2010, New Orleans, Poster W4066.
Cumming et al., "In vitro evaluation of a series of sodium carboxylates as dermal penetration enhancers," Int J Pharm 108:141-148 (1994).
Declaration of Dr. Thomas W. Leonard from European Patent Application EP; 00905186.3 (2007).
Doluisio et al., "Drug Absorption I: An in Situ Rat Gut Technique Yielding Realistic Absorption Rates," J. Pharm. Studies 58(10):1196-1200 (1969).
Drummond et al., "Clinical development of histone deacetylase inhibitors as anticancer agents," Annu. Rev. Pharmacol. Toxicol. 45:495-528 (2005).
European Food Safety Authority, "Scientific opinion on the use of ferric sodium EDTA as a source of iron added for nutritional purposes to foods for the general population (including food supplements) and to foods for particular nutritional uses", EFSA J. 8:1414 (2010).
Fatty Acids: Straight-Chain Saturated, downloaded from; http://lipidlibrary.aocs.org/Lipids/fa_branc/index.htm on Nov. 21, 2014.
Fernandez et al., "Comparative study on digestive lipase activities on the self emulsifying excipient Labrasol®, medium chain glycerides and PEG esters," Biochim. Biophys. Acta 1771:633-640 (2007).
Gennaro, "Remington: The Science and Practice of Pharmacy," 19th Edition, Mack Publishing Co., p. 1618 (1995).
Goodnough et al., "Erythropoietin, iron, and erythropolesis," Blood 96:823-833 (2000).
Grohganz et al., "Development and in vitro evaluation of a liposome based implant formulation for the decapeptide cetrorelix," Eur. J. Pharm. Biopharm. 59:439-448 (2004).
Hahn, "Chemotherapy Dose Calculation and Administration in Exotic Animal Species," Sem. Avian Exotic Pet Med. 14:193-198 (2005).
Hematopoietic and Blood Clotting Relationship Formulation, Remedy Manual 2007, 99. 946, 951-954.
Herbst "Gonadoptropin-Releasing Hormone Antagonist" Curr. Opin. Pharmacol. 2003 vol. 3 No. 6 pp. 660-666.
Hild et al., "The ability of a gonadotropin-releasing hormone antagonist, acyline, to prevent irreversible infertility induced by the indenopyridine, CDB-4022, in adult male rats: the role of testosterone," Biol. Reproduction 71:348-358 (2004).
Hovgaard "Insulin Stabilization and Gastrointestinal Absorption" Ph.D Thesis. The University of Utah. 1991. pp. 1-218.
Jewell et al., "The effect of conjugated linoleic acid and medium-chain fatty acids on transepithelial calcium transport in human intestinal-like Caco-2 cells," Br. J. Nutr. 89:639-647 (2003).
Jiang et al., "Betidamino acid scan of the GnRH antagonist acyline," J. Med. Chem. 40:3739-3748 (1997).

(56) References Cited

OTHER PUBLICATIONS

Jiang et al., "GnRH antagonists: a new generation of long acting analogues incorporating p-ureido-phenylalanines at positions 5 and 6," J. Med. Chem. 44:453-467 (2000).

Kajii et al., "Fluorescence study of the membrane-perturbing action of sodium caprylate as related to promotion of druq absorption," J. Pharm. Sci. 77:390-392 (1988).

Kalweit et al. "Pulmonary Embolism: A Frequent Cause of Acute Fatality after Lung Resection" Eur. J. Cardio-thorac. Surg 1996 vol. 10 Issue 4 pp. 242-247.

Kidron et al. "A Novel Per-Oral insulin formulation: proof of concept study in non-diabetic subjects" Diabetic Med 2004 vol. 21 p. 354.

Kishimoto, H. et al., "Efficacy and tolerability of once-weekly administration of 17.5mg risedronate in Japanese patients with involutional osteoporosis: a comparison with 2.5-mg once-daily dosage regimen", J. Bone Miner. Metab. 24: 405-413 (Sep. 1, 2006).

Kleinebudde "Roll compaction/dry granulation: pharmaceutical applications" Eur. J. Pharm. Biopham. 2004 vol. 58 Issue 2 pp. 317-326.

Lambent Technologies, "Technical Data Sheet for Lumulse L-4, Lumulse L-12, and Lumulse L-23", pp. 1-2 (2004).

Lambent Technologies, "Material Safety Data Sheet for Lumulse L-12", pp. 1-3 (2004).

Leonard et al. "Promoting absorption of drugs in humans using medium-chain fatty acid-based solid dosage forms: GIPET™" Expert Opinion on Drug Delivery 2006 vol. 3 pp. 685-692.

Leonard et al., MER-101 tablets: A bioavailability study of a novel oral formulation of zoledronic acid, Oct. 24, 2007, printed from http://www.merrionpharma.com/archive/mer101_poster_eortc.24oct07.pdf, Google date sheet of entry into the internet included, 2 paQes.

Lesnyak, "Medicamental methods of treating osteoporosis," Gynecology, vol. 7 (2005); accessed at www.consilium-medicum.com/article/7685.

Lin, Xiao et al "Release-controlling absorption enhancement of enterally administered Ophiopogon japonicus polysaccharide by sodium caprate in rats" Journal of Pharmaceutical Sciences 2006 vol. 95 No. 11 pp. 2534-2542.

Lindmark et al., "Mechanism of Absorption Enhancement in Humans After Rectal Administration of Ampicillin in Suppositories Containing Sodium Caprate," Pharm. Res. 14(7):930-935 (1997).

Lindmark et al., "Mechanisms of Absorption Enhancement by Medium Chain Fatty Acids in Intestinal Epithelial Caco-2 Cell Monolayers," J. Pharmacol. Exp. Ther. 275(2):958-964 (1995).

Louisa OO et al "Self-assembling PEG-p(CL-co_TMC) copolymers for oral delivery of poorly water-soluble drugs: a case study with risperidone" Journal of Controlled Release, 2005, vol. 102, No. 3, pp. 657-668.

Jones MC et al "pH-Sensitive Unimolecular Polymeric Micelles: Synthesis of a Novel Drug Carrier" Bioconjugate Chemistry, 2003, vol. 14, No. 4, pp. 774-781.

\* cited by examiner

SEQUENCE LISTING

```
<160> NUMBER OF SEQ ID NOS: 10

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Heloderma suspectum

<400> SEQUENCE: 2

His Ser Asp Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 3
<211> LENGTH: 39
<212> TYPE: PRT
<213> ORGANISM: Heloderma suspectum

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 4
<211> LENGTH: 33
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (1)..(1)
<223> OTHER INFORMATION: This residue is L-His, imidazopropionyl, alpha-
      hydroxy-histidine, D-His, desamino-His, 2-amino-His, beta-hydroxy-
      His, homo-His, N-alpha-acetyl-His, N-alpha-formyl-His, alpha-
      fluoromethyl-His, alpha-methyl-His, 3-pyridyl-Ala, 2-pyridyl-Ala,
      or 4-pyridyl-Ala
<220> FEATURE:
<221> NAME/KEY: SITE
<222> LOCATION: (2)..(2)
<223> OTHER INFORMATION: This residue is Ala, Gly, Val, Leu, Ile, Thr,
      Ser, Lys, Aib, (1-aminocyclopropyl) carboxylic acid, (1-
      aminocyclobutyl) carboxylic acid (CA), (1-aminocyclopentyl) CA,
      (1-aminocyclohexyl) CA, (1-aminocycloheptyl) CA, or
<220> FEATURE:
<221> NAME/KEY: SITE
<222> LOCATION: (6)..(6)
<223> OTHER INFORMATION: This residue is Lys or Phe
<220> FEATURE:
<221> NAME/KEY: SITE
<222> LOCATION: (10)..(10)
<223> OTHER INFORMATION: This residue is Val or Leu
<220> FEATURE:
<221> NAME/KEY: SITE
<222> LOCATION: (12)..(12)
<223> OTHER INFORMATION: This residue is Ser, Arg, Asn, Gln, or Glu
<220> FEATURE:
<221> NAME/KEY: SITE
<222> LOCATION: (13)..(13)
<223> OTHER INFORMATION: This residue is Tyr or Gln
<220> FEATURE:
<221> NAME/KEY: SITE
<222> LOCATION: (14)..(14)
<223> OTHER INFORMATION: This residue is Leu, Lys, or Met
<220> FEATURE:
<221> NAME/KEY: SITE
<222> LOCATION: (16)..(16)
<223> OTHER INFORMATION: This residue is Gly, Glu, Lys, or Aib
<220> FEATURE:
<221> NAME/KEY: SITE
<222> LOCATION: (17)..(17)
<223> OTHER INFORMATION: This residue is Gln, Glu, or Arg
<220> FEATURE:
<221> NAME/KEY: SITE
<222> LOCATION: (18)..(18)
<223> OTHER INFORMATION: This residue is Ala or Lys
<220> FEATURE:
```

```
<221> NAME/KEY: SITE
<222> LOCATION: (19)..(19)
<223> OTHER INFORMATION: This residue is Ala or Val
<220> FEATURE:
<221> NAME/KEY: SITE
<222> LOCATION: (20)..(20)
<223> OTHER INFORMATION: This residue is Val, His, Lys or Arg
<220> FEATURE:
<221> NAME/KEY: SITE
<222> LOCATION: (24)..(24)
<223> OTHER INFORMATION: This residue is Ala, Glu, or Arg
<220> FEATURE:
<221> NAME/KEY: SITE
<222> LOCATION: (25)..(25)
<223> OTHER INFORMATION: This residue is Trp or His
<220> FEATURE:
<221> NAME/KEY: SITE
<222> LOCATION: (28)..(28)
<223> OTHER INFORMATION: This residue is Glu, Asn, Gly, Gln, or Arg
<220> FEATURE:
<221> NAME/KEY: SITE
<222> LOCATION: (29)..(29)
<223> OTHER INFORMATION: This residue is Gly, Aib, or absent
<220> FEATURE:
<221> NAME/KEY: SITE
<222> LOCATION: (30)..(30)
<223> OTHER INFORMATION: This residue is Arg, Gly, Lys, or absent
<220> FEATURE:
<221> NAME/KEY: SITE
<222> LOCATION: (31)..(31)
<223> OTHER INFORMATION: This residue is Gly, Ala, Glu, Pro, Lys, Arg,
     or absent
<220> FEATURE:
<221> NAME/KEY: SITE
<222> LOCATION: (32)..(32)
<223> OTHER INFORMATION: This residue is Ser, Gly, Ala, Glu, Gln, Pro,
     Arg, or absent
<220> FEATURE:
<221> NAME/KEY: SITE
<222> LOCATION: (33)..(33)
<223> OTHER INFORMATION: This residue is Gly or absent

<400> SEQUENCE: 4

Xaa Xaa Glu Gly Thr Xaa Thr Ser Asp Xaa Ser Xaa Xaa Xaa Glu Xaa
 1               5                  10                  15

Xaa Xaa Xaa Xaa Lys Phe Ile Xaa Xaa Leu Val Xaa Xaa Xaa Xaa Xaa
            20                  25                  30

Xaa

<210> SEQ ID NO 5
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (20)..(20)
<223> OTHER INFORMATION: This amino acid residue is covalently attached
     to a substituent
<220> FEATURE:
<221> NAME/KEY: SITE
<222> LOCATION: (31)..(31)
<223> OTHER INFORMATION: This amino acid residue is covalently attached
     to a substituent

<400> SEQUENCE: 5

His Xaa Glu Gly Thr Phe Thr Ser Asp Val Ser Ser Tyr Leu Glu Gly
 1               5                  10                  15
```

Gln Ala Ala Lys Glu Phe Ile Ala Trp Leu Val Arg Gly Arg Lys
            20                  25                  30

```
<210> SEQ ID NO 6
<211> LENGTH: 33
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (21)..(21)
<223> OTHER INFORMATION: This amino acid residue is covalently attached
      to a substituent
<220> FEATURE:
<221> NAME/KEY: SITE
<222> LOCATION: (30)..(30)
<223> OTHER INFORMATION: This amino acid residue is covalently attached
      to a substituent

<400> SEQUENCE: 6
```

His Xaa Glu Gly Thr Phe Thr Ser Asp Val Ser Ser Tyr Leu Glu Glu
1               5                   10                  15

Gln Ala Ala Arg Lys Phe Ile Gly Trp Leu Val Arg Gly Lys Gly Glu
            20                  25                  30

Gly

```
<210> SEQ ID NO 7
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (1)..(1)
<223> OTHER INFORMATION: This residue (Xaa7) is L-His,
      (S)-2-Hydroxy-3-(1H-imidazol-4-yl)-propionic acid, D-His,
      desamino-His, Nalpha-acetyl-His, or Nalpha-formyl-His
<220> FEATURE:
<221> NAME/KEY: SITE
<222> LOCATION: (2)..(2)
<223> OTHER INFORMATION: This residue (Xaa8) is Ala, Ser, Aib, (1-
      aminocyclopropyl) carboxylic acid, or (1-aminocyclobutyl)
      carboxylic acid
<220> FEATURE:
<221> NAME/KEY: SITE
<222> LOCATION: (10)..(10)
<223> OTHER INFORMATION: This residue (Xaa16) is Val or Leu
<220> FEATURE:
<221> NAME/KEY: SITE
<222> LOCATION: (12)..(12)
<223> OTHER INFORMATION: This residue (Xaa18) is Ser or Arg
<220> FEATURE:
<221> NAME/KEY: SITE
<222> LOCATION: (13)..(13)
<223> OTHER INFORMATION: This residue (Xaa19) is Tyr or Gln
<220> FEATURE:
<221> NAME/KEY: SITE
<222> LOCATION: (14)..(14)
<223> OTHER INFORMATION: This residue (Xaa20) is Leu or Met
<220> FEATURE:
<221> NAME/KEY: SITE
<222> LOCATION: (16)..(16)
<223> OTHER INFORMATION: This residue (Xaa22) is Gly or Glu
<220> FEATURE:
<221> NAME/KEY: SITE
<222> LOCATION: (17)..(17)
<223> OTHER INFORMATION: This residue (Xaa23) is Gln, Glu, or Arg
<220> FEATURE:
```

```
<221> NAME/KEY: SITE
<222> LOCATION: (19)..(19)
<223> OTHER INFORMATION: This residue (Xaa25) is Ala or Val
<220> FEATURE:
<221> NAME/KEY: SITE
<222> LOCATION: (20)..(20)
<223> OTHER INFORMATION: This residue (Xaa26) is Arg or Lys
<220> FEATURE:
<221> NAME/KEY: SITE
<222> LOCATION: (21)..(21)
<223> OTHER INFORMATION: This residue (Xaa27) is Glu or Leu
<220> FEATURE:
<221> NAME/KEY: SITE
<222> LOCATION: (24)..(24)
<223> OTHER INFORMATION: This residue (Xaa30) is Ala or Glu
<220> FEATURE:
<221> NAME/KEY: SITE
<222> LOCATION: (25)..(25)
<223> OTHER INFORMATION: This residue (Xaa31) is Trp or His
<220> FEATURE:
<221> NAME/KEY: SITE
<222> LOCATION: (27)..(27)
<223> OTHER INFORMATION: This residue (Xaa33) is Val or Arg
<220> FEATURE:
<221> NAME/KEY: SITE
<222> LOCATION: (28)..(28)
<223> OTHER INFORMATION: This residue (Xaa34) is Arg, Lys, His, Asn, or
     Gln
<220> FEATURE:
<221> NAME/KEY: SITE
<222> LOCATION: (29)..(29)
<223> OTHER INFORMATION: This residue (Xaa35) is Gly or Aib

<400> SEQUENCE: 7

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Lys Lys
            20                  25                  30

<210> SEQ ID NO 8
<211> LENGTH: 31
<212> TYPE: PRT
<213> ORGANISM: ARTIFICIAL
<220> FEATURE:
<223> OTHER INFORMATION: Based on human GLP-1
<220> FEATURE:
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (30)..(30)
<223> OTHER INFORMATION: This amino acid residue is covalently attached
     to a substituent
<220> FEATURE:
<221> NAME/KEY: SITE
<222> LOCATION: (31)..(31)
<223> OTHER INFORMATION: This amino acid residue is covalently attached
     to a substituent

<400> SEQUENCE: 8

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30

<210> SEQ ID NO 9
<211> LENGTH: 31
<212> TYPE: PRT
<213> ORGANISM: ARTIFICIAL
<220> FEATURE:
<223> OTHER INFORMATION: Based on human GLP-1
<220> FEATURE:
```

```
<221> NAME/KEY: SITE
<222> LOCATION: (2)..(2)
<223> OTHER INFORMATION: This amino acid residue is Aib
<220> FEATURE:
<221> NAME/KEY: SITE
<222> LOCATION: (30)..(30)
<223> OTHER INFORMATION: This amino acid residue is covalently attached
      to a substituent
<220> FEATURE:
<221> NAME/KEY: SITE
<222> LOCATION: (31)..(31)
<223> OTHER INFORMATION: This amino acid residue is covalently attached
      to a substituent

<400> SEQUENCE: 9

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Lys
            20                  25                  30

<210> SEQ ID NO 10
<211> LENGTH: 31
<212> TYPE: PRT
<213> ORGANISM: ARTIFICIAL
<220> FEATURE:
<223> OTHER INFORMATION: GLP-1 agonist based on from human GLP-1
<220> FEATURE:
<221> NAME/KEY: SITE
<222> LOCATION: (2)..(2)
<223> OTHER INFORMATION: Aib
<220> FEATURE:
<221> NAME/KEY: SITE
<222> LOCATION: (30)..(30)
<223> OTHER INFORMATION: This amino acid residue is covalently attached
      to a substituent
<220> FEATURE:
<221> NAME/KEY: SITE
<222> LOCATION: (31)..(31)
<223> OTHER INFORMATION: This amino acid residue is covalently attached
      to a substituent

<400> SEQUENCE: 10

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30
```

TABLETS COMPRISING GLP-1 AGONIST AND ENTERIC COATING

CROSS-REFERENCE TO RELATED APPLICATIONS

This application is a 35 U.S.C. § 371 National Stage application of International Application PCT/EP2016/051795 (published as WO 2016/120378), filed Jan. 28, 2016, which claims priority to European Patent Applications 15188737.9, filed Oct. 7, 2015, 15162589.4, filed Apr. 7, 2015, PCT/EP2015/057442, filed Apr. 7, 2015 and 15153000.3, filed Jan. 29, 2015; the contents of all above-named applications are incorporated herein by reference.

The present invention relates to solid pharmaceutical compositions for oral administration comprising a GLP-1 agonist and an enteric coating as well as uses thereof.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Jun. 27, 2017, is named "140092US01_Sequence_Listing" and is 10 kilobytes in size.

BACKGROUND

Many pathological states caused by deficiencies in or complete failure of the production of certain macromolecules (e.g. proteins and peptides) are treated with an invasive and inconvenient parenteral administration of therapeutic macromolecules. One example hereof is administration of GLP-1 in the treatment of type 2 diabetes.

The oral route is desirable for administration due to its non-invasive nature and has a great potential to decrease the patient's discomfort related to administration of a drug substance and to increase patient compliance with administration of a drug substance. However, several problems exist; such as the enzymatic degradation in the gastrointestinal tract and limited permeability over the gastrointestinal membrane leading to insufficient and variable absorption. At present no products for oral delivery of GLP-1 agonists have been marketed.

Provision of a solid oral dosage form which would facilitate oral administration of GLP-1 is desirable. The advantages of solid oral dosage forms over other dosage forms include ease of manufacture, storage and administration. There may also be advantages relating to convenience of administration increasing patient compliance.

However, oral administration of GLP-1 agonists is challenged by poor bioavailability of GLP-1 agonists. Thus, new compositions providing improved oral bioavailability of GLP-1 agonists are desired.

SUMMARY

In some embodiments the present invention relates to tablets for oral administration comprising a GLP-1 agonist, an absorption enhancer which is a salt of capric acid, and an enteric coating as well as uses thereof.

In some embodiments the present invention relates to a solid pharmaceutical composition comprising i) a core comprising a salt of a medium-chain fatty acid and a GLP-1 agonist; and ii) a first coating which dissolves at pH 6.0 or higher, such as at pH 6.5 or higher, or pH 7.0 or higher.

In some embodiments the present invention relates to a solid pharmaceutical composition comprising i) a core comprising a salt of a medium-chain fatty acid and a GLP-1 agonist; and ii) a first coating consisting of an anionic copolymer coating, wherein said anionic copolymer coating comprises methacrylate copolymer, and wherein said methacrylate copolymer comprises a) 10-30% w/w methyl methacrylate, b) 50-70% w/w methyl acrylate, and c) 5-15% w/w methacrylic acid.

In some embodiments the present invention relates to a method for producing a solid pharmaceutical composition as defined in any one of the preceding embodiments, wherein said method comprises the steps of preparing a tablet core and applying a coating completely surrounding said tablet core, wherein said coating is an anionic copolymer coating obtained from a dispersion comprising between 25-35% w/w, such as 30% w/w, methacrylate copolymer as defined in any one of the preceding embodiments.

In some embodiments the present invention relates to a solid pharmaceutical composition as defined in any one of the preceding embodiments for use as a medicament, such as for use treatment or prevention of type 2 diabetes or obesity.

DESCRIPTION

In some embodiments the present invention relates to solid pharmaceutical composition, such as tablets, for oral administration comprising GLP-1, sodium caprate and an enteric coating as well as uses thereof. Enteric coated solid dosage forms pass through the stomach and release the drug substance when the target pH/site is reached in the intestine.

The present inventors surprisingly found that tablets comprising GLP-1 and an anionic copolymer coating, such as the enteric coating comprising FS30D as described herein, provide improved oral bioavailability of GLP-1. FS30D dissolves at pH 7 or higher according to information from the manufacturer (EUDRAGIT® FS 30 D as sold by Evonik Industries, Essen, Germany, in 2014; see http://eudragit.evonik.com/product/eudragit/en/products-services/eudragit-products/enteric-formulations/fs-30-d/pages/default.aspx); thus, release of the tablet core in the stomach is avoided.

Surprisingly, a pharmaceutical composition of the present invention in the form of a tablet with a coating comprising FS30D provided improved oral bioavailability of a GLP-1 agonist of 2.7% when tested in dogs (see Example 1 herein). In comparison, tablets comprising the same GLP-1 agonist and coated with the enteric coating Acryl-EZE 93A were tested in dogs and resulted a lower oral bioavailability of the GLP-1 agonist of 0.4% (see Example 4 herein). This formulation was also found to give low bioavailability in humans.

In some embodiments the present invention relates to a solid pharmaceutical composition comprising i) a core comprising a salt of a medium-chain fatty acid and a GLP-1 agonist; and ii) a first coating which dissolves at pH 6.0 or higher, such as at pH 6.5 or higher, or pH 7.0 or higher.

In some embodiments the present invention relates to a solid pharmaceutical composition comprising i) a core comprising a salt of a medium-chain fatty acid and a GLP-1 agonist; and ii) a first coating consisting of an anionic copolymer coating, wherein said anionic copolymer coating comprises methacrylate copolymer, and wherein said methacrylate copolymer comprises a) 10-30% w/w methyl methacrylate, b) 50-70% w/w methyl acrylate, and c) 5-15% w/w methacrylic acid.

Absorption Enhancer

The solid pharmaceutical composition comprises an absorption enhancer. The absorption enhancer may comprise a salt of a medium-chain fatty acid. As used herein the term medium-chain fatty acid refers to a saturated fatty acid consisting of 6-14 carbon atoms, such as 8-12 carbon atoms. The absorption enhancer may be a salt of capric acid. Capric acid may also be referred to as decanoic acid ($CH_3(CH_2)_8COOH$). The salt of capric acid may be sodium caprate (i.e. $CH_3(CH_2)_8COONa$). The solid pharmaceutical composition may comprise a salt of capric acid.

In some embodiments the solid pharmaceutical composition comprises at least 40% w/w, such as at least 50% w/w or at least 60% w/w, absorption enhancer. In some embodiments the solid pharmaceutical composition comprises at least 50-90% w/w, such as 55-85% w/w or 60-80% w/w, absorption enhancer.

Coating

The solid pharmaceutical composition of the invention comprises a core (e.g. a tablet core or a capsule) and at least one coating (also referred to herein as a first coating). In a particular embodiment the solid pharmaceutical composition comprises more than one core (e.g. minitablets, optionally comprised in larger unit, such as a tablet or a capsule) and at least one coating (e.g. located on the surface of each core and/or on the surface of the larger unit). The solid pharmaceutical composition may comprise an additional sub-coat (also referred to herein as a second coating) and/or a top-coat (also referred to herein as a third coating). The term "coating" as used herein refers to a substantially continuous layer surrounding the core of the solid pharmaceutical composition. The coating may be a continuous layer surrounding the core of the solid pharmaceutical composition. In some embodiments the coated solid composition of the invention comprises less than 10% w/w water. Coatings, such as enteric coatings or immediate release coatings, may be prepared according to methods well known in the art. In some embodiments the amount of coating to be applied is calculated based on the weight of the existing unit onto which the coating is to be applied, e.g. the core; for example, if a core of 500 mg is to be applied 5% of a coating then the amount of coating to be applied is calculated as 5%*500 mg which is 25 mg dry weight of the coating.

In some embodiments the term "comprise" when used in relation to an ingredient in a coating refers to the coating comprising at least 30% w/w, such as at least 30% w/w, at least 40% w/w or at least 50% w/w, or such as at least 55% w/w, at least 60% w/w or at least 65% w/w, of said ingredient.

First Coating

The solid pharmaceutical composition of the invention comprises a first coating. The first coating is a continuous layer surrounding the core of the solid pharmaceutical composition.

In some embodiments the first coating dissolves at pH 6.0 or higher, such as at pH 6.5 or higher, pH 7.0 or higher, or pH 7.2 or higher. Thus, the first coating may be resistant to dissolution at below pH 5.5, such as below pH 6.0, below pH 6.5, or below pH 7.0.

In some embodiments the first coating is an enteric coating. An enteric coating controls release of the part of the solid pharmaceutical composition surrounded by the enteric coating (e.g. the tablet core) to the surrounding environment; specifically, the enteric coating ensures that there is no contact between said part and the surrounding environment until a certain pH is reached in the surrounding environment. The site of release of the part of the solid pharmaceutical composition surrounded by the enteric coating may be customized depending on the ability of the enteric coating to resist dissolution in a specific pH range. In some embodiments the term "enteric coating" as used herein refers to a coating which i) does not dissolve in gastric fluid in humans or ii) dissolves at pH 6.0 or higher, such as at pH 6.5 or higher, or pH 7.0 or higher. In some embodiments the first coating dissolves at pH 6.0 or higher, such as at pH 6.5 or higher, or at pH 7.0 or higher.

In some embodiments the first coating comprises an anionic copolymer coating. The anionic copolymer coating may comprise at least 60% w/w, such as i) at least 70% w/w, at least 80% w/w, or at least 90% w/w, or ii) about 99% w/w, anionic copolymer. The first coating may comprise at least 40% w/w, such as at least 50% w/w, at least 60% w/w, or at least 70% w/w, anionic copolymer coating. In some embodiments the first coating is an anionic copolymer coating.

The solid pharmaceutical composition may comprise at least 2% w/w, such as 3-10% w/w, of said first coating.

Concentration of an ingredient in a coating (e.g. given as % w/w), unless otherwise specified, refers to the concentration of the ingredient in the final solid form of the coating. In some embodiments ratios between different monomers in a polymer referred to herein are given as molar ratios. The first coating may have a weight average molar mass of at least 100,000 g/mol, such as at least 150,000 g/mol, or at least 250,000 g/mol.

The first coating may comprise methacrylate copolymer. The first coating may comprise a copolymer derived from the monomers a) methyl methacrylate, b) methyl acrylate, and c) methacrylic acid. The first coating may comprise a copolymer derived from the monomers a) 10-40% methyl methacrylate, b) 50-80% methyl acrylate, and c) 5-15% methacrylic acid. The methacrylate copolymer may be derived from the monomers a) 10-40% methyl methacrylate, b) 50-80% methyl acrylate, and c) 5-15% methacrylic acid. The first coating may comprise a copolymer derived from the monomers a) 20-35% methyl methacrylate, b) 60-75% methyl acrylate, and c) 5-15% methacrylic acid. The first coating may comprise a copolymer derived from the monomers a) 30% methyl methacrylate, b) 70% methyl acrylate, and c) 10% methacrylic acid. The first coating may comprise a total of at least 70% w/w, such as at least 75% w/w or at least 80% w/w, of a copolymer derived from the monomers a) methyl methacrylate, b) methyl acrylate, and c) methacrylic acid.

The first coating may comprise a copolymer derived from the monomers methyl acrylate, methyl methacrylate and methacrylic acid, such as derived from at least 50 methyl acrylate, at least 20% methyl methacrylate, and at least 5% methacrylic acid. In some embodiments the first coating comprises the following copolymer:

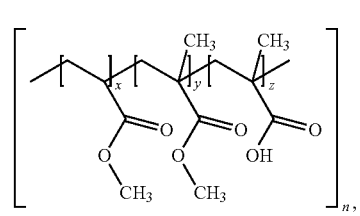

(Chem. 6)

wherein x=7, y=3, z=1 and n has an average of about 1000, such as 1080. In some embodiments the first coating comprises poly(methyl acrylate-co-methyl methacrylate-comethacrylic acid) 7:3:1. In some embodiments the first coating comprises at least 40% w/w poly (methyl acrylate-co-methyl methacrylate-co-methacrylic acid) 7:3:1.

A coating comprising poly (methyl acrylate-co-methyl methacrylate-co-methacrylic acid) 7:3:1 may be prepared using Eudragit® FS 30 D (as sold by Evonik Industries, Essen, Germany, in 2014). In some embodiments the first coating comprises FS30D. In some embodiments the first coating comprises FSD30. As used herein the term "FS30D" refers to a solid coating composition prepared by mixing at least 75% w/w, such as at least 80% w/w or such as 87% w/w, Eudragit® FS 30 D (as sold by Evonik Industries, Essen, Germany, in 2014) and at least 10% w/w, such as 13% w/w, PlasAcryl™ T20 (as sold by Evonik Industries, Essen, Germany, in 2014). In some embodiments the term "FS30D" refers to a solid coating obtained by Method 3a herein. The first coating may comprise at least 50% w/w or at least 60% w/w FS30D. The first coating may comprise at least 70% w/w, or at least 80% w/w, FS30D.

The first coating may, in addition to FS30D, comprise a copolymer derived from the monomers methacrylic acid and ethyl acrylate, such as derived from at least 40% methacrylic acid and at least 40% ethyl acrylate (referred to herein as poly(methacrylic acid-co-ethyl acrylate)). The poly(methacrylic acid-co-ethyl acrylate) may be derived from 40-60% methacrylic acid monomers and 40-60% ethyl acrylate monomers. In some embodiments the first coating, in addition to FS30D, comprises poly(methacrylic acid-co-ethyl acrylate) 1:1.

In some embodiments the first coating, in addition to FS30D, comprises the following copolymer:

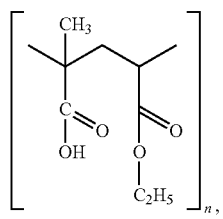

(Chem. 7)

wherein n an average of about 2000, such as 1900 or 1860. In some embodiments the first coating, in addition to FS30D, comprises L30D-55. A coating comprising L30D-55 may be prepared using Eudragit® L 30 D-55 (as sold by Evonik Industries, Essen, Germany, in 2014).

In some embodiments the first coating comprises i) poly (methyl acrylate-co-methyl methacrylate-co-methacrylic acid) 7:3:1 and ii) poly(methacrylic acid-co-ethyl acrylate) 1:1 in a ratio between i) and ii) of about 80:20 (w/w). In some embodiments the first coating comprises FS30D: L30D-55 80:20. As used herein the term "FS30D:L30D-55 80:20" refers to a solid coating composition prepared by mixing i) at least 50% w/w, such as at least 60% w/w or such as 69% w/w, Eudragit® FS 30 D (as sold by Evonik Industries, Essen, Germany, in 2014), ii) at least 10% w/w, such as at least 12% w/w or such as 17% w/w, Eudragit® L 30 D-55 (as sold by Evonik Industries, Essen, Germany, in 2014), iii) at least 3% w/w, such as at least 8% w/w or such as 13% w/w, PlasAcryl™ T20 (as sold by Evonik Industries, Essen, Germany, in 2014), and iv) 0.1-8% w/w, such as 0.5-3% w/w or 1.3% w/w, triethylcitrate, wherein the ratio between Eudragit® FS 30 D and Eudragit® L 30 D-55 is 80:20 (w/w). In some embodiments the term "FS30D:L30D-55 80:20" refers to a coating obtained by Method 3b herein, wherein the ratio between Eudragit® FS 30 D and Eudragit® L 30 D-55 is 80:20 (w/w).

In some embodiments the first coating comprises i) poly (methyl acrylate-co-methyl methacrylate-co-methacrylic acid) 7:3:1 and ii) poly(methacrylic acid-co-ethyl acrylate) 1:1 in a ratio between i) and ii) of about 50:50 (w/w). In some embodiments the first coating comprises FS30D: L30D-55 50:50. As used herein the term "FS30D:L30D-55 50:50" refers to a solid coating composition prepared mixing i) at least 35% w/w, such as at least 40% w/w or such as 43% w/w, Eudragit® FS 30 D (as sold by Evonik Industries, Essen, Germany, in 2014), ii) at least 35% w/w, such as at least 40% w/w or such as 43% w/w, Eudragit® L 30 D-55 (as sold by Evonik Industries, Essen, Germany, in 2014), iii) at least 5% w/w, such as at least 10% w/w or such as 13% w/w, PlasAcryl™ T20 (as sold by Evonik Industries, Essen, Germany, in 2014), and iv) 0.1-8% w/w, such as 0.5-3% w/w or 1.3% w/w, triethylcitrate, wherein the ratio between Eudragit® FS 30 D and Eudragit® L 30 D-55 is 50:50 (w/w). In some embodiments the term "FS30D:L30D-55 50:50" refers to a coating obtained by Method 3b herein, wherein the ratio between Eudragit® FS 30 D and Eudragit® L 30 D-55 is 50:50 (w/w).

The first coating may comprise 50% w/w or less, such as 25% w/w or less, or 20% w/w or less, L30D-55. The first coating may comprise at least 50% w/w FS30D and 50% w/w or less L30D-55. The first coating may comprise FS30D and L30D-55 in a ratio of about 50:50 or about 80:20.

The first coating may comprise S100. As used herein the term "S100" refers to a composition comprising poly(methacrylic acid-co-methyl methacrylate) 1:2. A product suitable to prepare a coating comprising S100 may be obtained from Evonik industries, Essen, Germany, in the form of the product sold as Eudragit® S100 in 2014. In some embodiments the term "S100" refers to a solid coating obtained by Method 3c herein.

The first coating may comprise L100. As used herein the term "L100" refers to a composition comprising poly(methacrylic acid-co-methyl methacrylate) 1:1. A product suitable to prepare a coating comprising L100 may be obtained from Evonik industries, Essen, Germany, in the form of the product sold as Eudragit® L 100 in 2014.

As used herein the term "Acryl-EZE 93A" refers to a composition comprising at least 50% w/w poly(methacrylic acid-co-ethyl acrylate) 1:1. A product suitable to prepare a coating comprising Acryl-EZE 93A may be obtained from Colorcon, Pa., USA, in the form of the product sold as product code 93A18597 in 2014. As used herein the term "Acryl-EZE 93O" refers to a solid coating comprising poly(methacrylic acid-co-ethyl acrylate) 1:1, such as at least 50% w/w poly(methacrylic acid-co-ethyl acrylate) 1:1. A product suitable to prepare an Acryl-EZE 93O coating may be obtained from Colorcon, Pa., USA, in the form of the product sold as product code 93O18509 in 2014. In some embodiments the term "Acryl-EZE", "Acryl-EZE 93A" or "Acryl-EZE 93O" refer to a solid coating obtained by Method 3d herein.

The compositions of the coatings described herein, such as the first coating, may be added additional water before being applied as a coating onto the core of the solid pharmaceutical composition.

Optional Second Coating: Sub-Coat

The solid pharmaceutical composition may comprise a second coating located between the core and the first coating. The second coating may be a substantially continuous layer surrounding the core of the solid pharmaceutical composition. The second coating may be an immediate release coating. As used herein the term "immediate release coating" refers to a thin coating which dissolves independently of the pH of the surroundings.

Specifically, the second coating may comprise Opadry Clear. As used herein the term "Opadry Clear" refers to a composition prepared using Opadry® Clear 03K19229 (as sold by Colorcon, Pa., USA, in 2014). In some embodiments the term "Opadry Clear" refers to a solid coating obtained by Method 2a herein.

Alternatively, the second coating may comprise Opadry II Yellow. As used herein the term "Opadry II Yellow" refers to a composition comprising polyvinyl alcohol. A product suitable to prepare a coating comprising Opadry II Yellow may be obtained from Colorcon, Pa., USA, in the form of the product sold as product code 85F32410 in 2014. In some embodiments the term "Opadry II Yellow" when used in connection with a second coating refers to a solid coating obtained by Method 2b herein.

Alternatively, the second coating may comprise Pharmacoat. A product suitable to prepare a coating comprising Pharmacoat may be obtained from Shin-Etsu, Tokyo, Japan, in the form of the product sold as Pharmacoat® 603 in 2014. In some embodiments the term "Pharmacoat" refers to a solid coating obtained by Method 2c herein.

Alternatively, the second coating may comprise Kollicoat. A product suitable to prepare a coating comprising Kollicoat may be obtained from BASF, Ludwigshafen, Germany, in the form of the product sold as Kollicoat® IR in 2014. In some embodiments the term "Kollicoat" refers to a solid coating obtained by Method 2d herein.

The second coating may comprise Opadry Clear, Opadry II Yellow, Pharmacoat or Kollicoat. The second coating may consist of Opadry Clear, Opadry II Yellow, Pharmacoat or Kollicoat.

The solid pharmaceutical composition according to any one of the preceding embodiments, wherein said solid pharmaceutical composition comprises at least 0.5% w/w, such as 0.1-5% w/w, of said second coating.

Optional Third Coating: Top-Coat

The solid pharmaceutical composition may comprise a third coating which, if present, is the outer coating of the solid pharmaceutical composition. In some embodiments the third coating surrounds at least said core and said first coating. The third coating may be a substantially continuous layer surrounding at least the core and the first coating of the solid pharmaceutical composition. The third coating may be a film coating.

The third coating may be an immediate release coating.

Specifically, the third coating may be Opadry White. As used herein the term "Opadry White" refers to a composition prepared using Opadry® White obtained from Colorcon, Pa., USA, in the form of the product sold as product code 03F180011 in 2014. In some embodiments the term "Opadry White" refers to a solid coating obtained by Method 4a herein.

Alternatively, the third coating may comprise Opadry II Yellow. As used herein the term "Opadry II Yellow" refers to a composition comprising polyvinyl alcohol. A product suitable to prepare a coating comprising Opadry® II Yellow may be obtained from Colorcon, Pa., USA, in the form of the product sold as product code 85F32410 in 2014. In some embodiments the term "Opadry II Yellow" when used in connection with a third coating refers to a solid coating obtained by Method 4b herein.

Alternatively, the third coating may comprise a copolymer based on methacrylic acid and ethyl acrylate, such as copolymer based on at least 40% methacrylic acid and at least 40% ethyl acrylate. In some embodiments the third coating comprises poly(methacrylic acid-co-ethyl acrylate) 1:1. In some embodiments the third coating comprises the compound Chem. 7, wherein n an average of about 2000, such as 1900 or 1860. In some embodiments the first coating may comprise poly(methacrylic acid-co-ethyl acrylate) 1:1. In some embodiments the first coating comprises the following compound:

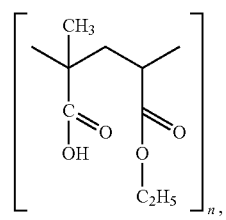

(Chem. 7)

wherein n an average of about 2000, such as 1900 or 1860. As used herein the term "L30D-55" refers to a composition comprising at least 60% w/w, such as at least 80% w/w, poly(methacrylic acid-co-ethyl acrylate) 1:1. A coating comprising L30D-55 may be prepared using Eudragit® L 30 D-55 (as sold by Evonik, Essen, Germany, in 2014). In some embodiments a coating comprising L30D-55 is prepared by mixing at least 75% w/w, such as 80% w/w, Eudragit® L 30 D-55 (as sold by Evonik, Essen, Germany, in 2014) and at least 15% w/w, such as 20% w/w, PlasAcryl™ HTP20 (as sold by Evonik Industries, Essen, Germany, in 2014). In some embodiments the term "L30D-55" when used in connection with a third coating refers to a solid coating obtained by Method 4c herein.

The third coating may comprise Opadry White, Opadry II Yellow or L30D-55. The third coating may consist of Opadry White, Opadry II Yellow or L30D-55.

The solid pharmaceutical composition may comprise at least 0.1% w/w, such as 0.5-8% w/w or 1-5% w/w, of said third coating.

In some embodiments the solid pharmaceutical composition comprises a first coating obtained from a dispersion comprising between 25-35% w/w, such as 30% w/w, methacrylate copolymer, wherein said methacrylate copolymer is as defined herein.

The solid pharmaceutical composition may comprise said first coating, said second coating and said third coating. The solid pharmaceutical composition may comprise said first coating and said second coating and not said third coating. The solid pharmaceutical composition may comprise said first coating and said third coating and not said second coating. The solid pharmaceutical composition may comprise said first coating and neither said second coating nor said third coating.

Tablet Composition

The present invention relates to a solid pharmaceutical composition which may be for oral administration. In some embodiments the solid pharmaceutical composition is in the form of a tablet, a capsule, minitablets. The solid pharmaceutical composition may be in the form of a tablet.

The solid pharmaceutical composition may comprise one or more pharmaceutically acceptable excipients, such as a filler and/or a lubricant. The filler may be sorbitol. In some embodiments the solid pharmaceutical composition comprises less than 35% w/w sorbitol, such as 10-30% w/w sorbitol. The lubricant may be stearic acid. In some embodiments the solid pharmaceutical composition comprises less than 10% w/w, such as 0.1-5% w/w, lubricant.

The total weight of the solid pharmaceutical composition, such as the tablet, may be in the range of 100 mg to 1500 mg. The total weight of the solid pharmaceutical composition may be in the range of 100-1200 mg, such as 200-1000 mg, 400-800 mg, or 600-900 mg. A tablet may have a total weight of at least 100 mg, such as 100-1200 mg, 400-800 mg or 600-900 mg. A minitablet may have a total weight of 2-50 mg, such as 3-20 mg. In some embodiments the term "total weight" as used herein refers to the weight of the tablet including core and coating(s).

The solid pharmaceutical composition may comprise granules, e.g. of sodium caprate, which have been manufactured by granulation. The term "granulate" may refer to one or more granules. The term "granule" may refer to particles gathered into larger particles.

In some embodiments the composition of the invention does not comprise a protease inhibitor. In some embodiments the composition of the invention does not comprise a Bowman-Birk Inhibitor.

Manufacturing of Tablets

The solid pharmaceutical composition, such as tablets, of the invention may be prepared according to methods known in the art. The solid pharmaceutical composition may be prepared as described in the examples herein. In some embodiments at least part of the ingredients for the core of the solid pharmaceutical composition, such as the tablet core, may be granulated prior to being compressed into tablets.

To prepare a dry blend of tabletting material, the various components are weighed, optionally delumped and then combined. The mixing of the components may be carried out until a homogeneous blend is obtained.

To compress the tabletting material into a solid oral dosage form, for example a tablet, a tablet press may be used. In a tablet press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. An Example of tablet press is, but is not limited to, the Fette 102i (Fette GmbH). In some embodiments the tablet is prepared by exerting a compression force in the range of 5-25 kN.

In some embodiments the invention relates to a method for producing a solid pharmaceutical composition as defined herein, wherein said method comprises the steps of preparing a tablet core and applying a coating completely surrounding said tablet core, wherein said coating is an anionic copolymer coating obtained from a dispersion comprising between 25-35% w/w, such as 30% w/w, methacrylate copolymer as defined herein.

Functional Features

Oral Bioavailability

In some embodiments the solid pharmaceutical compositions of the invention provide an improved oral bioavailability of the GLP-1 agonist. Generally, the term bioavailability refers to the fraction of an administered dose of the drug substance, such as a GLP-1 agonist, that reaches the systemic circulation unchanged. By definition, when a drug substance is administered intravenously, its bioavailability is 100%. However, when the drug substance is administered via other routes (such as orally), its bioavailability decreases (due to degradation and/or incomplete absorption and first-pass metabolism). Knowledge about bioavailability is important when calculating dosages for non-intravenous routes of administration of a drug substance. A plasma concentration versus time plot is made after both oral and intravenous administration. The absolute bioavailability is the (AUC-oral divided by dose), divided by (AUC-intravenous divided by dose).

Stability of GLP-1 Oral Bioavailability Performance after Storage

Tablets coated according to the present invention were manufactured in a tablet batch and stored at 5° C. Oral bioavailability of GLP-1 agonists in dogs was determined from a fraction of the tablets 2 weeks after end of manufacturing of the tablet batch; determination of oral bioavailability is repeated for the same tablet batch e.g. i) after some weeks of continued storage at 5° C. and ii) after further some weeks of continued storage at 5° C. Oral bioavailability may be determined according to Method 8 described herein.

GLP-1 Agonist

The solid pharmaceutical composition of the invention comprises a GLP-1 agonist. The GLP-1 agonist may be a GLP-1 peptide or an analogue or derivative thereof. The GLP-1 agonist may be a derivative of a GLP-1 analogue. The GLP-1 agonist may be human GLP-1, exendin-4 or an analogue or derivative thereof. The GLP-1 agonist may be acylated. The GLP-1 agonist may comprise a peptide comprising no more than 10 substitutions, deletions and/or additions of amino acids relative to human GLP-1 or exendin-4. In particular, the GLP-1 agonist may comprise a peptide comprising no more than 8, such as no more than 6, no more than 5, or no more than 4, substitutions, deletions and/or additions of amino acids relative to human GLP-1 or exendin-4. The GLP-1 agonist may comprise a peptide comprising no more than 8 substitutions, deletions and/or additions of amino acids relative to human GLP-1.

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" (also referred to herein as a "GLP-1 agonist") may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to human GLP-1.

GLP-1 Peptides and Analogues

The term "GLP-1 peptide" as used herein refers to the human Glucagon-Like Peptide-1 (GLP-1(7-37)), the sequence of which is included in the sequence listing as SEQ ID NO: 1, or an analogue thereof. The peptide having the sequence of SEQ ID NO: 1 may also be designated "human GLP-1".

The term "GLP-1 analogue" or "analogue of GLP-1" as used herein refers to a peptide, or a compound, which is a variant of GLP-1(7-37) (SEQ ID NO: 1).

In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in human GLP-1(7-37) which corresponds to the amino acid residue which is changed (i.e., the corresponding position in human GLP-1), and to ii) the actual change.

In other words, a GLP-1 analogue is a GLP-1(7-37) peptide in which a number of amino acid residues have been changed when compared to human GLP-1(7-37) (SEQ ID NO: 1). These changes may represent, independently, one or more amino acid substitutions, additions, and/or deletions.

The following are non-limiting examples of suitable analogue nomenclature.

Analogues "comprising" certain specified changes may comprise further changes, when compared to SEQ ID NO: 1. In some embodiments the analogue "has" the specified changes.

As is apparent from the above examples, amino acid residues may be identified by their full name, their one-letter code, and/or their three-letter code. These three ways are fully equivalent.

The expressions "a position corresponding to" or "corresponding position" may be used to characterise the site of change in a variant GLP-1(7-37) sequence by reference to human GLP-1(7-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

Selected GLP-1 agonists are:

```
                 7    10         20         30    37
GLP-1(7-37):     HAE  GTFTSDVSSY LEGQAAKEFI AWLVKGRG
(SEQ ID NO: 1)
Exendin-4(1-39): HGE  GTFTSDLSKQ MEEEAVRLFI EWLKNGGPSSGAPPPS
(SEQ ID NO: 2)
Exendin-3(1-39): HSD  GTFTSDLSKQ MEEEAVRLFI EWLKNGGPSSGAPPPS
(SEQ ID NO: 3)
                 1    4          14         24    39
```

In case of non-natural amino acids such as Imp and/or Aib being included in the sequence, these may, for alignment purposes, be replaced with, e.g., X. If desired, X can later be manually corrected.

The term "peptide", as e.g. used in the context of the GLP-1 analogues of the derivatives of the invention, refers to a compound which comprises a series of amino acids interconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids.

In particular embodiments, the peptide is composed of at least five constituent amino acids, preferably composed of at least 10, at least 15, at least 20, at least 25, or most preferably composed of at least 28 amino acids.

In additional particular embodiments, the peptide a) is composed of, or b) consists of 29-33 amino acids. In some embodiments the peptide consists of 29, 30, or 31 amino acids. In some embodiments the peptide consists of 32, 33 or 34 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid), des-amino-histidine (alternative name imidazopropionic acid, abbreviated Imp), as well as the D-isomers of the proteinogenic amino acids. In what follows, all amino acids of the GLP-1 agonist (e.g. GLP-1 peptide) for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. In some embodiments the GLP-1 analogue comprises Formula I:

Xaa7-Xaa8-Glu-Gly-Thr-Xaa12-Thr-Ser-Asp-Xaa16-Ser-Xaa18-Xaa19-Xaa20-Glu-Xaa22-Xaa23-Xaa24-Xaa25-Xaa26-Lys-Phe-Ile-Xaa30-Xaa31-Leu-Val-Xaa34-Xaa35-Xaa36-Xaa37-Xaa38-Xaa39 (SEQ ID NO:4), wherein     Formula I:

Xaa7 is L-histidine, imidazopropionyl, α-hydroxy-histidine, D-histidine, desamino-histidine, 2-amino-histidine, β-hydroxy-histidine, homohistidine, Nα-acetyl-histidine, Nα-formyl-histidine, α-fluoromethyl-histidine, α-methyl-histidine, 3-pyridylalanine, 2-pyridylalanine, or 4-pyridylalanine;

Xaa8 is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa12 is Lys or Phe;
Xaa16 is Val or Leu;
Xaa18 is Ser, Arg, Asn, Gln, or Glu;
Xaa19 is Tyr or Gln;

Xaa20 is Leu, Lys, or Met;
Xaa22 is Gly, Glu, Lys, or Aib;
Xaa23 is Gln, Glu, or Arg;
Xaa24 is Ala or Lys;
Xaa25 is Ala or Val;
Xaa26 is Val, His, Lys or Arg;
Xaa30 is Ala, Glu, or Arg;
Xaa31 is Trp or His;
Xaa34 is Glu, Asn, Gly, Gln, or Arg;
Xaa35 is Gly, Aib, or absent;
Xaa36 is Arg, Gly, Lys, or absent;
Xaa37 is Gly, Ala, Glu, Pro, Lys, Arg, or absent;
Xaa38 is Ser, Gly, Ala, Glu, Gln, Pro, Arg, or absent; and
Xaa39 is Gly or absent.

In some embodiments the GLP-1 analogue is a GLP-1 analogue of Formula I. In some embodiments the GLP-1 analogue the peptide of Formula I is an analogue of GLP-1(7-37) (SEQ ID NO: 1). If Xaa38 of Formula I is absent, then Xaa39 of Formula I may also be absent. If Xaa37 of Formula I is absent, then Xaa38 and Xaa39 of Formula I may also be absent. If Xaa36 of Formula I is absent, then Xaa37, Xaa38, and Xaa39 of Formula I may also be absent. If Xaa35 of Formula I is absent, then Xaa36, Xaa37, Xaa38, and Xaa39 of Formula I may also be absent.

In some embodiments the GLP-1 analogue is a GLP-1 analogue of Formula I (SEQ ID NO:4), wherein Xaa7 is His; Xaa8 is Ala or Aib; Xaa12 is Lys or Phe; Xaa16 is Val; Xaa18 is Ser; Xaa19 is Tyr; Xaa20 is Leu or Lys; Xaa22 is Glu, Gly or Lys; Xaa23 is Glu or Gln; Xaa24 is Ala or Lys; Xaa25 is Ala or Val; Xaa26 is Lys or Arg; Xaa30 is Ala or Glu; Xaa31 is Trp or His; Xaa34 is Gly, Gln, or Arg; Xaa35 is Gly or absent; Xaa36 is Arg, Lys, or absent; Xaa37 is Gly, Lys, or absent; Xaa38 is Glu, Gln or absent; and Xaa39 is Gly or absent.

In some embodiments the GLP-1 analogue is a GLP-1 analogue of Formula I (SEQ ID NO:4), wherein Xaa7 is His; Xaa8 is Aib; Xaa12 is Phe; Xaa16 is Val; Xaa18 is Ser; Xaa19 is Tyr; Xaa20 is Leu; Xaa22 is Glu or Gly; Xaa23 is Gln; Xaa24 is Ala; Xaa25 is Ala; Xaa26 is Lys or Arg; Xaa30 is Ala or Glu; Xaa31 is Trp; Xaa34 is Arg; Xaa35 is Gly; Xaa36 is Arg or Lys; Xaa37 is Gly or Lys; Xaa38 is Glu or absent; and Xaa39 is Gly or absent.

GLP-1 Derivatives

The term "derivative" as used herein in the context of a GLP-1 agonist (e.g. GLP-1 peptide) means a chemically modified GLP-1 agonist, in which one or more substituents have been covalently attached to the constituent peptide (also referred to herein as a "GLP-1 derivative"). The substituent may also be referred to as a side chain. Thus, the term "derivative" as used herein in the context of a GLP-1 analogue means a chemically modified GLP-1 analogue, in which one or more substituents have been covalently attached to the peptide. The GLP-1 derivative may comprise a GLP-1 agonist (e.g. GLP-1 peptide) covalently attached by acylation to a substituent, wherein said substituent comprises a lipophilic moiety and optionally a distal aromatic group (e.g. 4-carboxyphenoxy).

In some embodiments the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the drug substance. Thus, the substituent, or side chain, as a whole is preferably referred to as an albumin binding moiety.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In another particular embodiment the albumin binding moiety comprises a portion which is particularly relevant for the albumin binding and thereby the protraction, which portion may accordingly be referred to as a protracting moiety. The protracting moiety may be near, preferably at, the terminal (or distal, or free) end of the albumin binding moiety, relative to its point of attachment to the peptide.

In a still further particular embodiment the albumin binding moiety comprises a portion between the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the constituent peptide (e.g. GLP-1 peptide) by acylation, i.e., via an amide bond formed between a carboxylic acid group thereof (of the albumin binding moiety, the protracting moiety, or the linker) and an amino group of the lysine residue. Additional or alternative conjugation chemistry includes alkylation, ester formation, or amide formation, or coupling to a cysteine residue, such as by maleimide or haloacetamide (such as bromo-/fluoro-/iodo-) coupling.

In some embodiments an active ester of the albumin binding moiety, preferably comprising a protracting moiety and a linker, is covalently linked to an amino group of a lysine residue, preferably the epsilon amino group thereof, under formation of an amide bond, as explained above.

Unless otherwise stated, when reference is made to an acylation of a lysine residue, it is understood to be to the epsilon-amino group thereof.

The term "fatty acid" refers to aliphatic monocarboxylic acids having from 4 to 28 carbon atoms, it is preferably un-branched, and it may be saturated or unsaturated.

The term "fatty diacid" refers to fatty acids as defined above but with an additional carboxylic acid group in the omega position. Thus, fatty diacids are dicarboxylic acids. The fatty diacid may comprise 14-22 carbon atoms.

Each of the two linkers of the derivative of the invention may comprise the following first linker element:

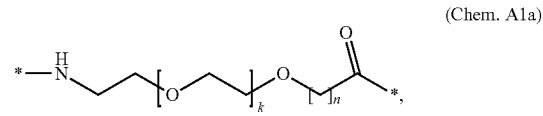
(Chem. A1a)

wherein k is an integer in the range of 1-5, and n is an integer in the range of 1-5.

In some embodiments, when k=1 and n=1, this linker element may be designated OEG, or a di-radical of 8-amino-3,6-dioxaoctanic acid, and/or it may be represented by the following formula:

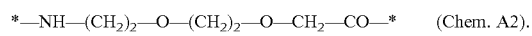
*—NH—(CH$_2$)$_2$—O—(CH$_2$)$_2$—O—CH$_2$—CO—*    (Chem. A2).

In some embodiments each linker of the derivative of the invention may further comprise, independently, a second linker element, preferably a Glu di-radical, such as Chem. B1:

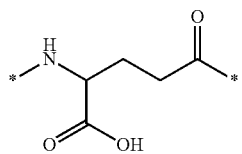

(Chem. B1)

wherein the Glu di-radical may be included p times, where p is an integer in the range of 1-3. Chem. B1 may also be referred to as gamma-Glu, or briefly gGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

As explained above, the GLP-1 derivatives may be double-acylated, i.e. two albumin binding moieties are covalently attached to the constituent peptide (e.g. GLP-1 peptide).

In some embodiments the two albumin binding moieties (i.e. the entire side chains) are similar, preferably substantially identical, or, most preferably, identical.

In some embodiments the two protracting moieties are similar, preferably substantially identical, or, most preferably, identical.

In some embodiments the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as the albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted hereinbelow, in which a known entire side chain of a known GLP-1 derivative was compared with a methyl ester thereof:

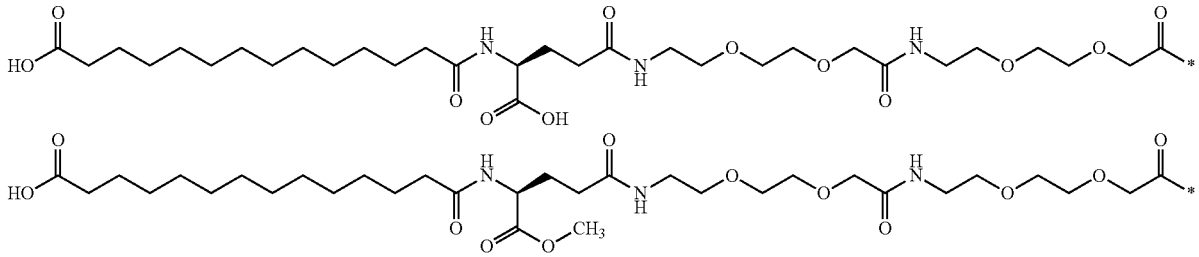

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

In some embodiments the GLP-1 derivative comprises a GLP-1 analogue, wherein the GLP-1 analogue comprises a first K residue and a second K residue selected from the group consisting of i) a first K residue at a position corresponding to position 26 of GLP-1(7-37) (SEQ ID NO: 1) and a second K residue at a position corresponding to position 37 of GLP-1(7-37); and ii) a first K residue at a position corresponding to position 27 of GLP-1(7-37) (SEQ ID NO: 1) and a second K residue at a position corresponding to position T of GLP-1(7-37), where T is an integer in the range of 7-37 except 18 and 27; wherein the first K residue is designated $K^F$, and the second K residue is designated $K^T$;

wherein the GLP-1 analogue comprises a maximum of ten amino acid changes as compared to GLP-1(7-37);

wherein the GLP-1 derivative comprises a first and a second protracting moiety attached to $K^F$ and $K^T$, respectively, via a first and a second linker, respectively, wherein the first and the second protracting moiety is selected from Chem. C1 and Chem. C2:

 Chem. C1:

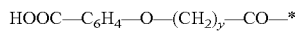 Chem. C2:

in which x is an integer in the range of 6-16, y is an integer in the range of 3-17; and the first and second linker comprises Chem. D5:

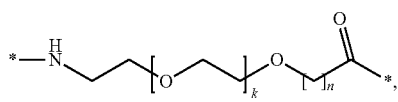 Chem. D5 wherein k is an integer in the range of 1-5, and n is an integer in the range of 1-5; or a pharmaceutically acceptable salt, amide, or ester thereof. In some embodiments the GLP-1 derivative comprises a GLP-1 analogue, wherein the GLP-1 analogue comprises a first K residue and a second K residue selected from the group consisting of i) a first K residue at a position corresponding to position 26 of GLP-1(7-37) (SEQ ID NO: 1) and a second K residue at a position corresponding to position 37 of GLP-1(7-37); and ii) a first K residue at a position corresponding to position 27 of GLP-1(7-37) (SEQ ID NO: 1) and a second K residue at a position corresponding to position T of GLP-1(7-37), where T is an integer in the range of 7-37 except 18 and 27; wherein the first K residue is designated $K^F$, and the second K residue is designated $K^T$; wherein the GLP-1 analogue comprises a maximum of ten amino acid changes as compared to GLP-1(7-37); wherein the GLP-1 derivative comprises a first and a second protracting moiety attached to $K^F$ and $K^T$, respectively, via a first and a second linker, respectively, wherein the first and the second protracting moiety is selected from Chem. 1 and Chem. 2:

 Chem. C1:

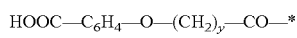 Chem. C2:

in which x is an integer in the range of 6-16, y is an integer in the range of 3-17; and the first and second linker comprises Chem. D5:

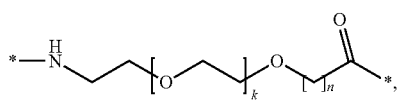 Chem. D5 wherein k is an integer in the range of 1-5, and n is an integer in the range of 1-5; or a pharmaceutically acceptable salt, amide, or ester thereof.

In some embodiments ($K^F$,$K^T$) are at positions corresponding to positions (26,37) of GLP-1(7-37) (SEQ ID NO: 1). In some embodiments ($K^F$,$K^T$) are at positions corresponding to positions (27,36) of GLP-1(7-37) (SEQ ID NO: 1).

In some embodiments the GLP-1 derivative comprises the protracting moiety Chem. C2. In some embodiments Chem. C2 is represented by Chem. C2a:

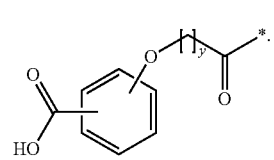 Chem. C2a

In some embodiments y of Chem. C2 or Chem. C2a is an odd number. In some embodiments y of Chem. 2 or Chem. 2a is an integer in the range of 9-11, such as 9, 10 or 11. In some embodiments Chem. C2 is represented by Chem. C2b, or Chem. C2c:

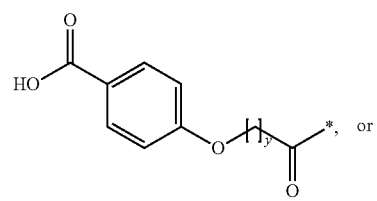 Chem. C2b

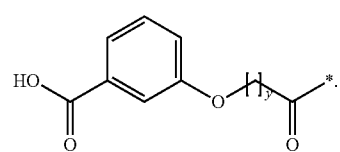 Chem. C2c

In some embodiments Chem. D5 is a first linker element. In some embodiments Chem. 5 is a first linker element. In some embodiments k of Chem. D5 is 1. In some embodiments n of Chem. D5 is 1. In some embodiments Chem. D5 is included m times, wherein m is an integer in the range of 1-10. In some embodiments m is 2. When m is not 1, then the Chem. D5 elements may be interconnected via amide bond(s).

In some embodiments the GLP-1 derivative further comprises a second linker element. In some embodiments the second linker element is a Glu di-radical. In some embodiments the second linker element is selected from Chem. E6, and/or Chem. E7:

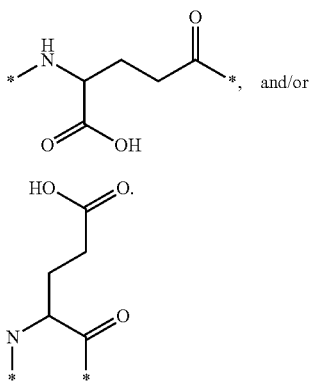

Chem. E6

Chem. E7 and/or

In some embodiments the second linker element is Chem. E6. In some embodiments the Glu di-radical is included p times, wherein p is an integer in the range of 1-2, such as 1 or 2. In some embodiments the second linker element comprises the Glu di-radical which is a radical of L-Glu. In some embodiments the second linker element comprises one or more Glu di-radicals and one or more Chem. D5 elements are interconnected via amide bond(s). In some embodiments the linker consists of m times Chem. D5 and p times the Glu di-radical. In some embodiments (m,p) is (2,2) or (2,1). In some embodiments (m,p) is (2,1). In some embodiments the m Chem. D5 elements and the p Glu di-radicals are interconnected via amide bonds.

In some embodiments the linker and the protracting moiety are interconnected via an amide bond. In some embodiments the linker and the GLP-1 analogue are interconnected via an amide bond. In some embodiments the linker is attached to the epsilon-amino group of the first or the second K residue.

The GLP-1 agonist may be semaglutide. Semaglutide may be prepared as disclosed in WO2006/097537, e.g. Example 4. Semaglutide may be referred to as $N^{6.26}$-{18[N-(17-carboxyheptadecanoyl)-L-γ-glutamyl]-10-oxo-3,6,12,15-tetraoxa-9,18-diazaoctadecanoyl}-[8-(2-amino-2-propanoic acid), 34-L-arginine]human glucagon-like peptide 1(7-37) (WHO Drug Information Vol. 24, No. 1, 2010).

The GLP-1 agonist may be Compound A which is $N^{ε26}${2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl}, $N^{ε37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib$^8$,Arg$^{34}$,Lys$^{37}$] GLP-1(7-37)-peptide and has the following structure:

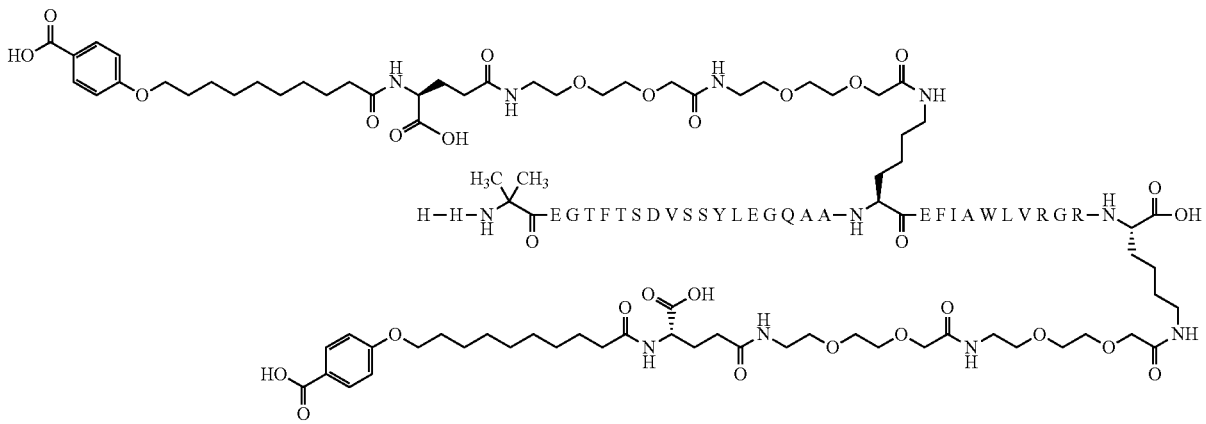

The amino acid sequence of compound A is set forth in SEQ ID NO: 5

Compound A may be prepared as disclosed in WO2011/080103, e.g. Example 2.

The GLP-1 agonist may be Compound B which is $N^{ε27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{ε36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Glu22,Arg26,Lys27, Glu30,Arg34,Lys36]-GLP-1-(7-37)-peptidyl-Glu-Gly and has the following structure:

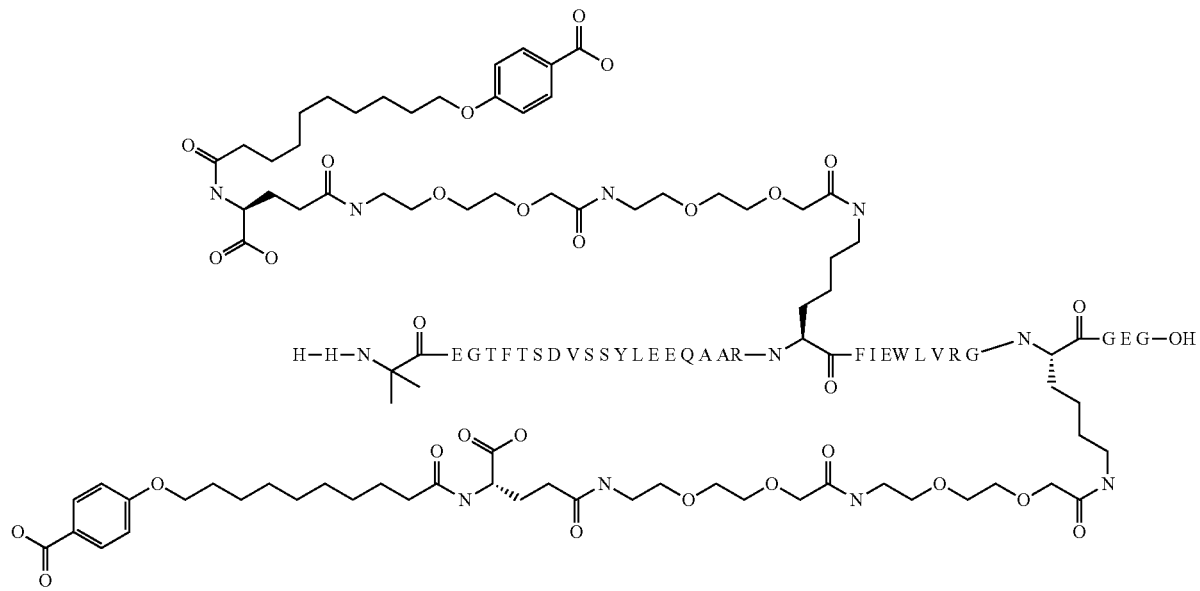

The amino acid sequence of compound B is set forth in SEQ ID NO:6
Compound B may be prepared as disclosed in WO2012/140117, e.g. Example 31. Compound B may also be illustrated as follows

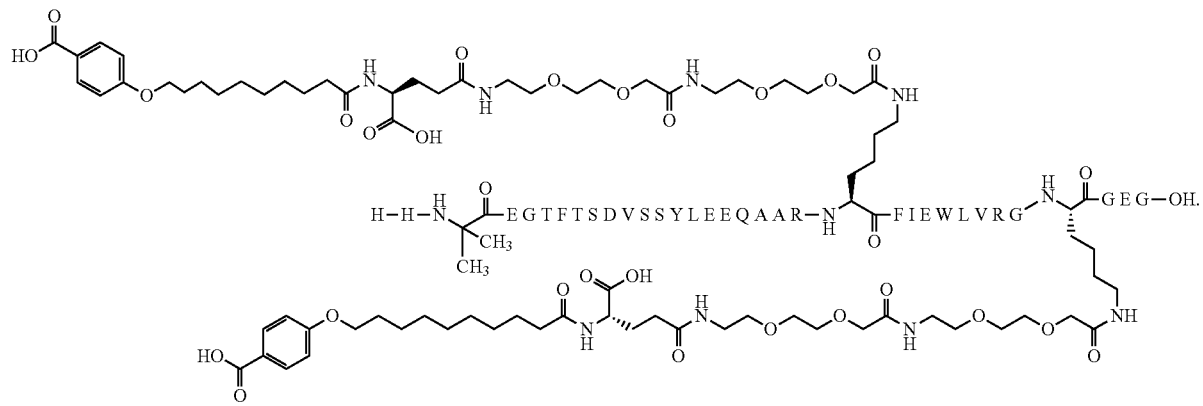

The amino acid sequence of compound B is set forth in SEQ ID NO:6

In some embodiments the GLP-1 agonist is a GLP-1 derivative (e.g. a derivative of a GLP-1 analogue) acylated with a side chain on the epsilon-amino group of a lysine at each of positions 36 and 37;
wherein each side chain individually comprises a protractor of formula:

HOOC—C$_6$H$_4$—O—(CH$_2$)$_y$—CO—*  Chem. 1:

where y is an integer in the range of 8-11, attached to epsilon-amino group of a lysine at position 36 and 37; and wherein the protractor is attached to the epsilon-amino group via a linker comprising
i) gGlu of the formula:

*—NH—CH(COOH)—(CH$_2$)$_2$—CO—*,  Chem. 3:

and
ii) a moiety of the formula:

*NH—(CH$_2$)$_2$—[O—(CH$_2$)$_2$]$_k$—O—[CH$_2$]$_n$—CO—*,  Chem. 5:

wherein k is an integer in the range of 1-5, and n is an integer in the range of 1-5; or a pharmaceutically acceptable salt, amide, or ester thereof.

In some embodiments, in the GLP-1 derivative of the invention, the linker, protractor, and peptide are connected via amide bonds at *. In some embodiments gGlu of the linker is connected to the protractor via amide bonds at *. In some embodiments gGlu of the linker is connected to the moiety of Chem. 5 via amide bonds at *. In some embodiments the moiety of Chem. 5 of the linker is connected to the peptide via amide bonds at *. In some embodiments the moiety of the formula defined by Chem. 5 is "OEG", i.e. n=k=1. In some embodiments the linker is "*-gGlu-OEG-OEG-**" connected to the protractor at * and connected to the peptide at **. In some embodiments the protractor has y=10 and is in para configuration. In some embodiments the protractor has y=9 and is in para configuration. In some embodiments the protractor has y=9 or y=10 and is in meta configuration.

In some embodiments the GLP-1 derivative comprises Formula II (SEQ ID NO:7):

Xaa7-Xaa8-Glu-Gly-Thr-Phe-Thr-Ser-Asp-Xaa16-
Ser-Xaa18-Xaa19-Xaa20-Glu-Xaa22-Xaa23-
Ala-Xaa25-Xaa26-Xaa27-Phe-Ile-Xaa30-Xaa31-
Leu-Xaa33-Xaa34-Xaa35-Lys36-Lys37(SEQ ID
NO:7), wherein                                  Formula II:

Xaa7 is L-histidine, (S)-2-Hydroxy-3-(1H-imidazol-4-yl)-propionic acid, D-histidine, desamino-histidine (desH), Nα-acetyl-histidine, or Nα-formyl-histidine;

Xaa8 is Ala, Ser, Aib, (1-aminocyclopropyl) carboxylic acid, or (1-aminocyclobutyl) carboxylic acid;
Xaa16 is Val or Leu;
Xaa18 is Ser or Arg;
Xaa19 is Tyr or Gln;
Xaa20 is Leu or Met;
Xaa22 is Gly or Glu;
Xaa23 is Gln, Glu, or Arg;
Xaa25 is Ala or Val;
Xaa26 is Arg or Lys;
Xaa27 is Glu or Leu;
Xaa30 is Ala, or Glu;
Xaa31 is Trp or His
Xaa33 is Val or Arg;
Xaa34 is Arg, Lys, His, Asn, or Gln; and
Xaa35 is Gly or Aib.

In some embodiments the GLP-1 derivative is a GLP-1 derivative of Formula II (SEQ ID NO:7), wherein Xaa7 is His; Xaa8 is Aib; Xaa16 is Val; Xaa18 is Ser; Xaa19 is Tyr; Xaa20 is Leu; Xaa22 is Gly or Glu; Xaa23 is Gln; Xaa25 is Ala; Xaa26 is Arg; Xaa27 is Glu; Xaa30 is Ala or Glu; Xaa31 is Trp; Xaa33 is Val; Xaa34 is Arg or Gln; and Xaa35 is Gly.

In some embodiments the GLP-1 derivative is a GLP-1 derivative of Formula II (SEQ ID NO:7), wherein Xaa7 is His; Xaa8 is Aib; Xaa16 is Val; Xaa18 is Ser; Xaa19 is Tyr; Xaa20 is Leu; Xaa22 is Glu; Xaa23 is Gln; Xaa25 is Ala; Xaa26 is Arg; Xaa27 is Glu; Xaa30 is Ala; Xaa31 is Trp; Xaa33 is Val; Xaa34 is Arg; and Xaa35 is Gly.

The GLP-1 agonist may be Compound C which is N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide and has the following structure:

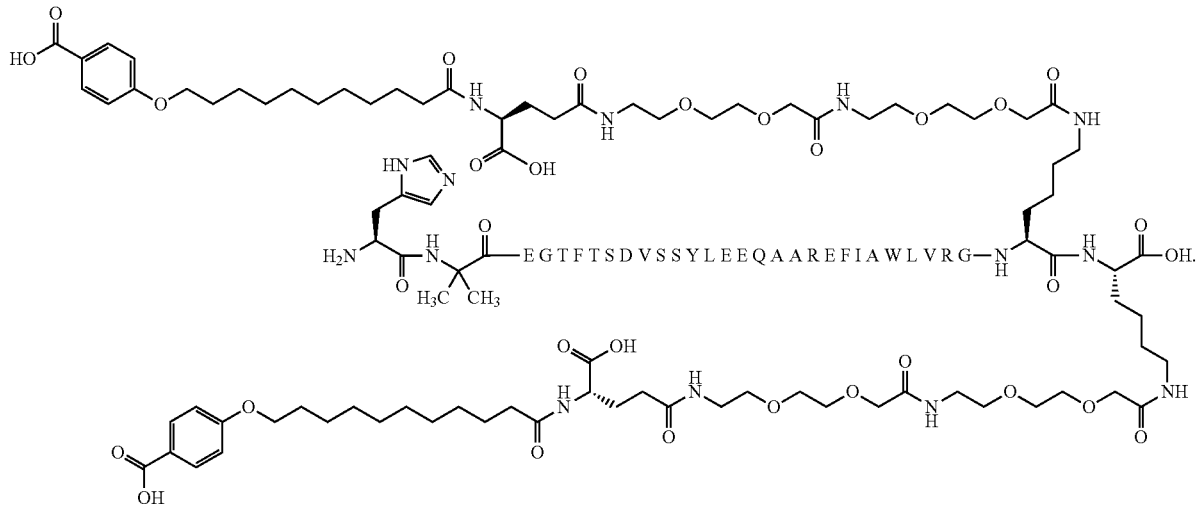

The amino acid sequence of compound C is set forth in SEQ ID NO: 8

Compound C may be prepared as disclosed in Example 1 of PCT/EP2015/057442.

The GLP-1 agonist may be Compound D which is N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide and has the following structure:

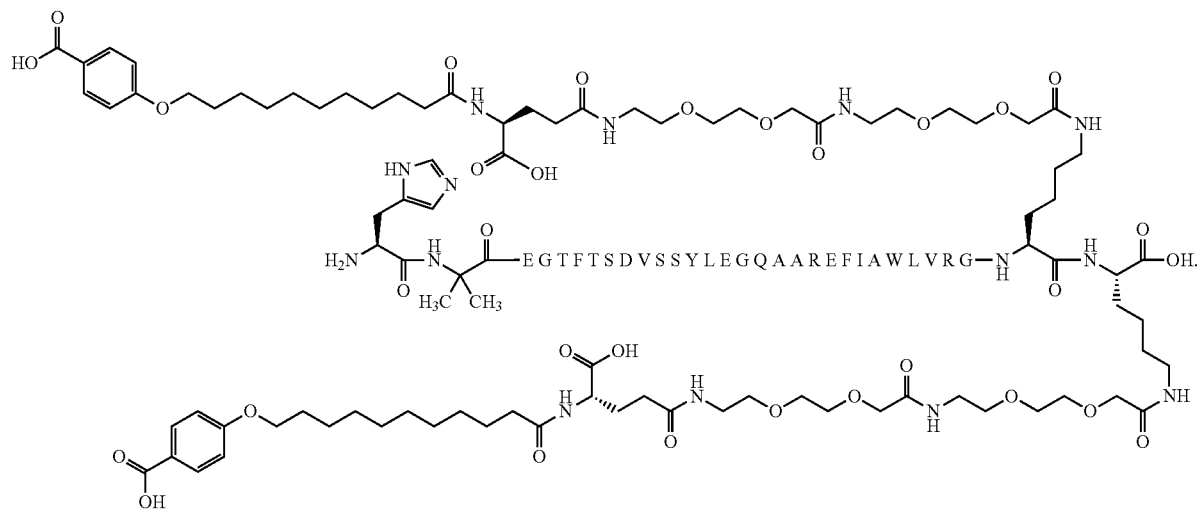

The amino acid sequence of compound D is set forth in SEQ ID NO: 9
Compound D may be prepared as disclosed in Example 2 of PCT/EP2015/057442. In some embodiments Compound C and Compound D may be prepared according to other methods known by a person skilled in the art.

The GLP-1 agonist may be Compound E which is N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8, Glu22,Arg26,Arg34,Lys36,Lys37]-GLP-1-(7-37)-peptide embodiment the GLP-1 agonist is selected from the group consisting of semaglutide, Compound A, Compound B, and Compound E.

The GLP-1 derivatives may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of GLP-1 derivatives may be determined using any suitable method. For example, LC-MS

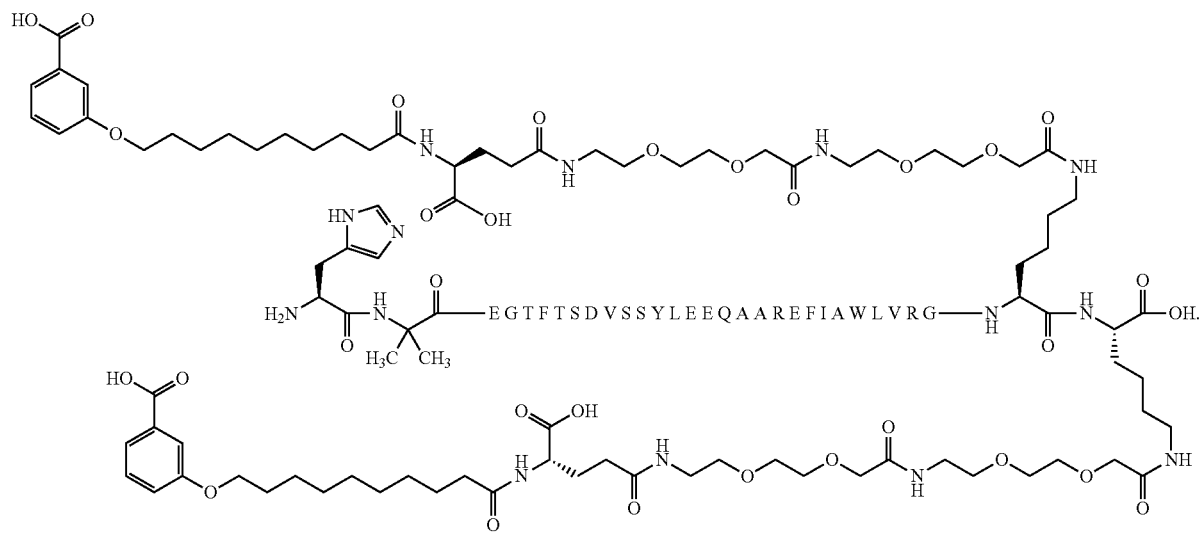

The amino acid sequence of compound E is set forth in SEQ ID NO: 10.
Compound E may be prepared as disclosed in e.g. WO2012/140117 or Example 35 of PCT/EP2015/057442.

In one embodiment the GLP-1 agonist is selected from the group consisting of semaglutide, Compound A, Compound B, Compound C, Compound D, and Compound E. In one (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoassay). General protocols for suitable RIA and ELISA assays are found in, e.g., WO 2009/030738 on p. 116-118.

The GLP-1 agonist may be in the form of a salt, ester or amide.

A non-limiting list of examples of GLP-1 agonists for use in the present invention may be found in WO 2006/097537, WO 2011/080103, WO2012/140117, and/or PCT/EP2015/057442. Methods for preparation of GLP-1 peptides of the present invention can for example be found in WO2006/097537, WO2011/080103, WO2012/140117, or PCT/EP2015/057442. Methods for preparation of such GLP-1 peptides as well as assays for characterizing such GLP-1 peptides, such as physical and chemical stability as well as potency and $T_{1/2}$ are provided in WO2006/097537, WO2011/080103, WO2012/140117, and PCT/EP2015/057442. Compound E may be prepared as disclosed in e.g. WO2012/140117 or Example 2 of PCT/EP2015/057442.

Indications

The present invention also relates to the solid pharmaceutical composition of the invention for use as a medicament.

In particular embodiments the solid pharmaceutical composition of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In some embodiments the indication is selected from the group consisting of (i)-(xiv), such as indications (i)-(viii), (x)-(xiii), and/or (xiv), and relates in one way or the other to diabetes.

In some embodiments the indication is selected from the group consisting of (i)-(iii) and (v)-(viii), such as indications (i), (ii), and/or (iii); or indication (v), indication (vi), indication (vii), and/or indication (viii).

In some embodiments the indication is (i). In some embodiments the indication is (v). In some embodiments the indication is (viii).

The following indications are particularly preferred: Type 2 diabetes, and/or obesity. In some embodiments the solid pharmaceutical composition of the invention is for use treatment or prevention of type 2 diabetes or obesity.

In some embodiments the invention is directed to a method for treatment or prevention of type 2 diabetes or obesity comprising administering a solid pharmaceutical composition as defined in any one of the preceding embodiments.

EMBODIMENTS OF THE INVENTION

The following are non-limiting embodiments of the invention:

Composition

1. A solid pharmaceutical composition comprising i) a core comprising a salt of a medium-chain fatty acid and a GLP-1 agonist; and ii) a first coating which dissolves at pH 6.0 or higher, such as at pH 6.5 or higher, or pH 7.0 or higher.

2. A solid pharmaceutical composition comprising i) a core comprising a salt of a medium-chain fatty acid and a GLP-1 agonist; and ii) a first coating consisting of an anionic copolymer coating, wherein said anionic copolymer coating comprises methacrylate copolymer, and wherein said methacrylate copolymer comprises a)

10-30% w/w methyl methacrylate, b) 50-70% w/w methyl acrylate, and c) 5-15% w/w methacrylic acid.

First Coating

3. The solid pharmaceutical composition according to any one of the preceding embodiments, wherein said first coating is an enteric coating.
4. The solid pharmaceutical composition according to any one of the preceding embodiments, wherein said first coating comprises at least 40% w/w, such as at least 50% w/w, at least 60% w/w, or at least 70% w/w, anionic copolymer coating.
5. The solid pharmaceutical composition according to any one of the preceding embodiments, wherein said first coating is an anionic copolymer coating.
6. The solid pharmaceutical composition according to any one of the preceding embodiments, wherein said first coating comprises methacrylate copolymer.
7. The solid pharmaceutical composition according to any one of the preceding embodiments, wherein said first coating dissolves at pH 6.0 or higher, such as at pH 6.5 or higher, or at pH 7.0 or higher.
8. The solid pharmaceutical composition according to any one of the preceding embodiments, wherein said solid pharmaceutical composition comprises at least 2% w/w, such as 3-10% w/w, of said first coating.

FS30D

9. The solid pharmaceutical composition according to any one of the preceding embodiments, wherein said first coating comprises a copolymer derived from the monomers a) methyl methacrylate, b) methyl acrylate, and c) methacrylic acid.
10. The solid pharmaceutical composition according to any one of the preceding embodiments, wherein said first coating comprises a copolymer derived from the monomers a) 10-40% methyl methacrylate, b) 50-80% methyl acrylate, and c) 5-15% methacrylic acid.
11. The solid pharmaceutical composition according to any one of the preceding embodiments, wherein said methacrylate copolymer is derived from the monomers a) 10-40% methyl methacrylate, b) 50-80% methyl acrylate, and c) 5-15% methacrylic acid.
12. The solid pharmaceutical composition according to any one of the preceding embodiments, wherein said first coating comprises a copolymer derived from the monomers a) 20-35% methyl methacrylate, b) 60-75% methyl acrylate, and c) 5-15% methacrylic acid.
13. The solid pharmaceutical composition according to any one of the preceding embodiments, wherein said first coating comprises a copolymer derived from the monomers a) 30% methyl methacrylate, b) 70% methyl acrylate, and c) 10% methacrylic acid.
14. The solid pharmaceutical composition according to any one of the preceding embodiments, wherein said first coating comprises a total of at least 70% w/w, such as at least 75% w/w or at least 80% w/w, of a copolymer derived from the monomers a) methyl methacrylate, b) methyl acrylate, and c) methacrylic acid.
15. The solid pharmaceutical composition according to any one of the preceding embodiments, wherein said first coating comprises FS30D, such as at least 50% w/w, at least 60% w/w, at least 70% w/w, or at least 80% w/w FS30D.

L30D-55

16. The solid pharmaceutical composition according to any one of the preceding embodiments, wherein said first coating comprises poly(methacrylic acid-co-ethyl acrylate) 1:1.
17. The solid pharmaceutical composition according to any one of the preceding embodiments, wherein said poly (methacrylic acid-co-ethyl acrylate) is derived from 40-60% methacrylic acid monomers and 40-60% ethyl acrylate monomers.
18. The solid pharmaceutical composition according to any one of the preceding embodiments, wherein said first coating comprises L30D-55, such as 50% w/w or less, 25% w/w or less, or 20% w/w or less, L30D-55.
19. The solid pharmaceutical composition according to any one of the preceding embodiments, wherein said first coating comprises at least 50% w/w FS30D and 50% w/w or less L30D-55.
20. The solid pharmaceutical composition according to any one of the preceding embodiments, wherein said first coating comprises FS30D and L30D-55 in a ratio of about 50:50 or about 80:20.

Sub-Coat

21. The solid pharmaceutical composition according to any one of the preceding embodiments, wherein said solid pharmaceutical composition comprises a second coating located between said core and said first coating.
22. The solid pharmaceutical composition according to any one of the preceding embodiments, wherein said second coating is an immediate release coating.
23. The solid pharmaceutical composition according to any one of the preceding embodiments, wherein said second coating comprises Opadry Clear, Opadry II Yellow, Pharmacoat or Kollicoat.
24. The solid pharmaceutical composition according to any one of the preceding embodiments, wherein said solid pharmaceutical composition comprises at least 0.5% w/w, such as 0.1-5% w/w, of said second coating.

Top-Coat

25. The solid pharmaceutical composition according to any one of the preceding embodiments, wherein said solid pharmaceutical composition comprises a further third coating surrounding and containing said core and said first coating.
26. The solid pharmaceutical composition according to any one of the preceding embodiments, wherein said third coating is an immediate release coating.
27. The solid pharmaceutical composition according to any one of the preceding embodiments, wherein said third coating comprises Opadry White, Opadry II Yellow or L30D-55.
28. The solid pharmaceutical composition according to any one of the preceding embodiments, wherein said solid pharmaceutical composition comprises at least 0.1% w/w, such as 0.5-8% w/w or 1-5% w/w, of said third coating.
29. The solid pharmaceutical composition according to any one of the preceding embodiments, wherein said solid pharmaceutical composition comprises said first coating, said second coating and said third coating.
30. The solid pharmaceutical composition according to any one of the preceding embodiments, wherein said solid pharmaceutical composition comprises said first coating and said second coating and not said third coating.
31. The solid pharmaceutical composition according to any one of the preceding embodiments, wherein said solid pharmaceutical composition comprises said first coating and said third coating and not said second coating.
32. The solid pharmaceutical composition according to any one of the preceding embodiments, wherein said solid pharmaceutical composition comprises said first coating and neither said second coating nor said third coating.

Form of Composition
33. The solid pharmaceutical composition according to any one of the preceding embodiments, wherein said solid pharmaceutical composition is in the form of a tablet.
34. The solid pharmaceutical composition according to any one of the preceding embodiments, wherein said solid pharmaceutical composition is in the form of a capsule or a minitablet.
35. The solid pharmaceutical composition according to any one of the preceding embodiments, wherein said solid pharmaceutical composition has a total weight in the range of 100-1200 mg, such as 200-1000 mg, 400-800 mg, or 600-900 mg.

Salt of a Medium-Chain Fatty Acid
36. The solid pharmaceutical composition according to any one of the preceding embodiments, wherein said salt of a medium-chain fatty acid is a salt of a saturated fatty acid consisting of 6-14 carbon atoms.
37. The solid pharmaceutical composition according to any one of the preceding embodiments, wherein said salt of a medium-chain fatty acid is a salt of capric acid.
38. The solid pharmaceutical composition according to any one of the preceding embodiments, wherein said salt of capric acid is sodium caprate.

GLP-1 Agonist
39. The solid pharmaceutical composition according to any one of the preceding embodiments, wherein said GLP-1 agonist is human GLP-1, exendin-4 or an analogue or derivative thereof.
40. The solid pharmaceutical composition according to any one of the preceding embodiments, wherein said GLP-1 agonist comprises a peptide comprising no more than 10 substitutions, deletions and/or additions of amino acids relative to human GLP-1 or exendin-4.
41. The solid pharmaceutical composition according to any one of the preceding embodiments, wherein said GLP-1 agonist comprises a peptide comprising no more than 8, such as no more than 6, no more than 5, or no more than 4, substitutions, deletions and/or additions of amino acids relative to human GLP-1 or exendin-4.
42. The solid pharmaceutical composition according to any one of the preceding embodiments, wherein said GLP-1 agonist is acylated.
43. The solid pharmaceutical composition according to any one of the preceding embodiments, wherein said GLP-1 agonist is a GLP-1 analogue of Formula I (SEQ ID NO:1) as defined herein.
44. The solid pharmaceutical composition according to any one of the preceding embodiments, wherein said GLP-1 agonist is semaglutide.
45. The solid pharmaceutical composition according to any one of the preceding embodiments, wherein said GLP-1 agonist is $N^{\epsilon 26}$\{2-[2-(2-\{2-[2-(2-\{(S)-4-Carboxy-4-[10-(4-carboxyphenoxy)decanoylamino]butyrylamino\}ethoxy)ethoxy]acetylamino\}ethoxy)ethoxy]acetyl\}, $N^{\epsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$^8$,Arg$^{34}$,Lys$^{37}$]GLP-1(7-37)-peptide (Compound A):

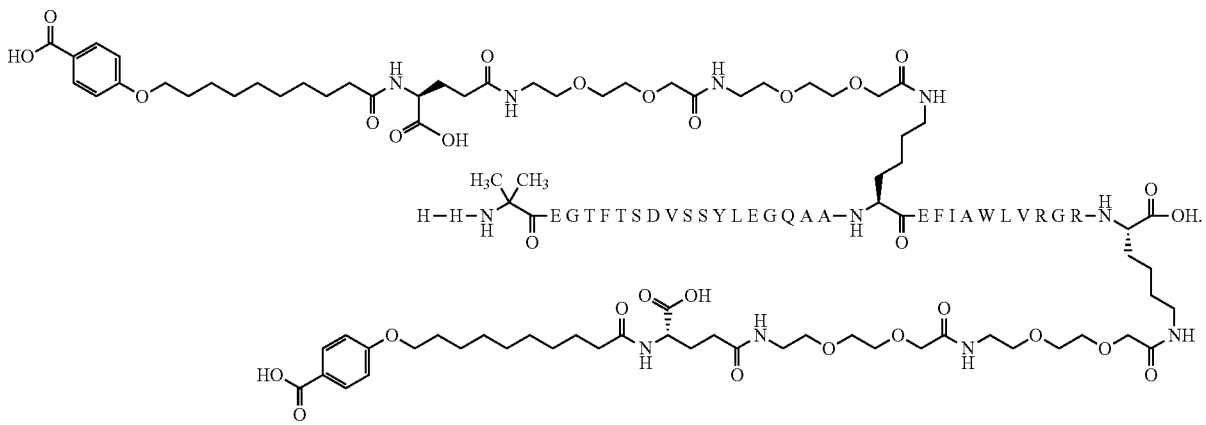

The amino acid sequence of compound A is set forth in SEQ ID NO: 5
46. The solid pharmaceutical composition according to any one of the preceding embodiments, wherein said GLP-1 agonist is $N^{\epsilon 27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl], $N^{\epsilon 36}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib8,Glu22,Arg26,Lys27,Glu30,Arg34,Lys36]-GLP-1-(7-37)-peptidyl-Glu-Gly (Compound B):

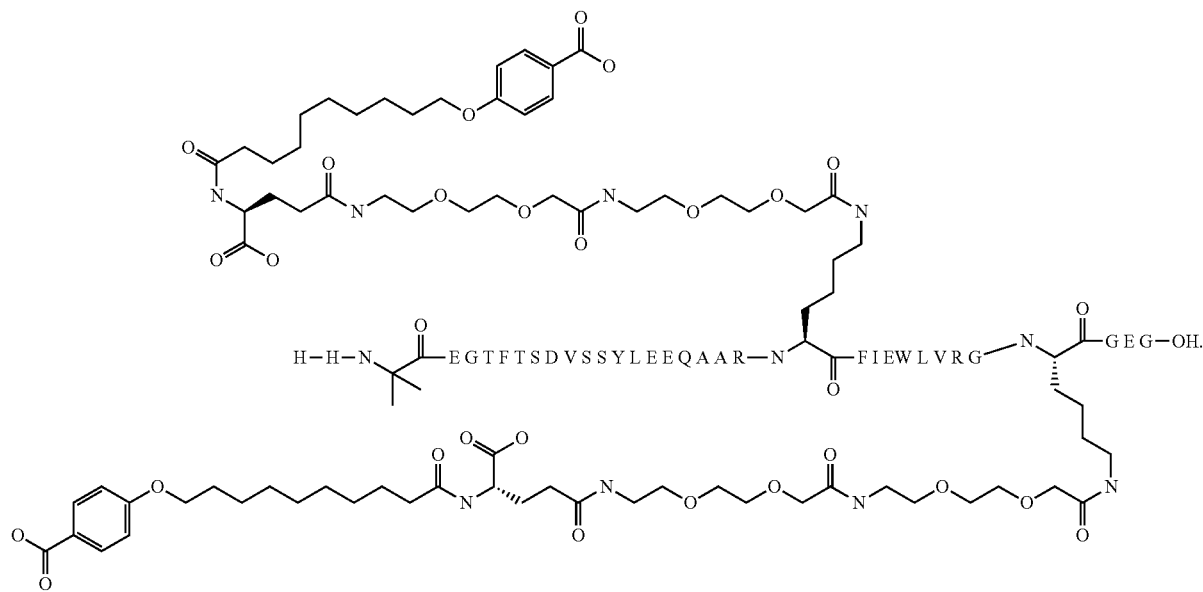

The amino acid sequence of compound B is set forth in SEQ ID NO:6

47. The solid pharmaceutical composition according to any one of the preceding embodiments, wherein said GLP-1 agonist is N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Compound C):

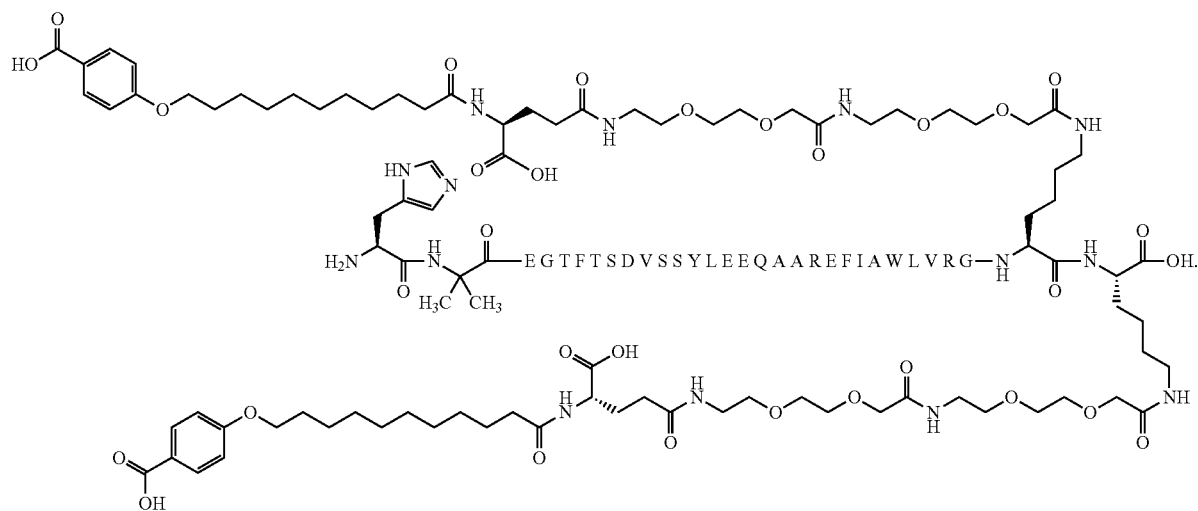

The amino acid sequence of compound C is set forth in SEQ ID NO: 8

48. The solid pharmaceutical composition according to any one of the preceding embodiments, wherein said GLP-1 agonist is N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Aib8,Arg26,Arg34,Lys36,Lys37]-GLP-1-(7-37)-peptide (Compound D):

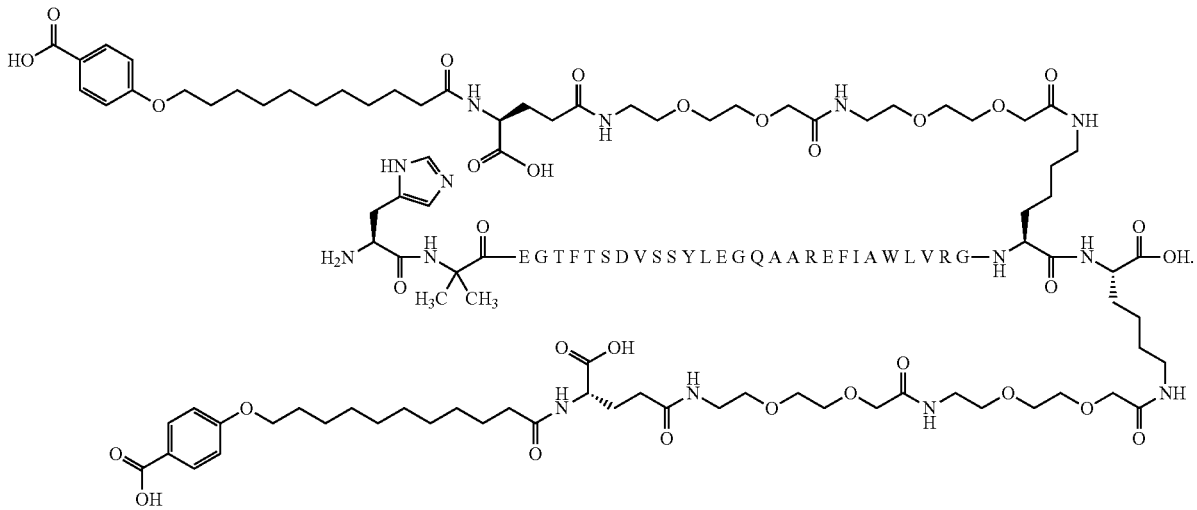

The amino acid sequence of compound D is set forth in SEQ ID NO: 9

49. The solid pharmaceutical composition according to any one of the preceding embodiments, wherein said GLP-1 agonist is N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Aib8,Glu22,Arg26,Arg34,Lys36,Lys37]-GLP-1-(7-37)-peptide (Compound E)

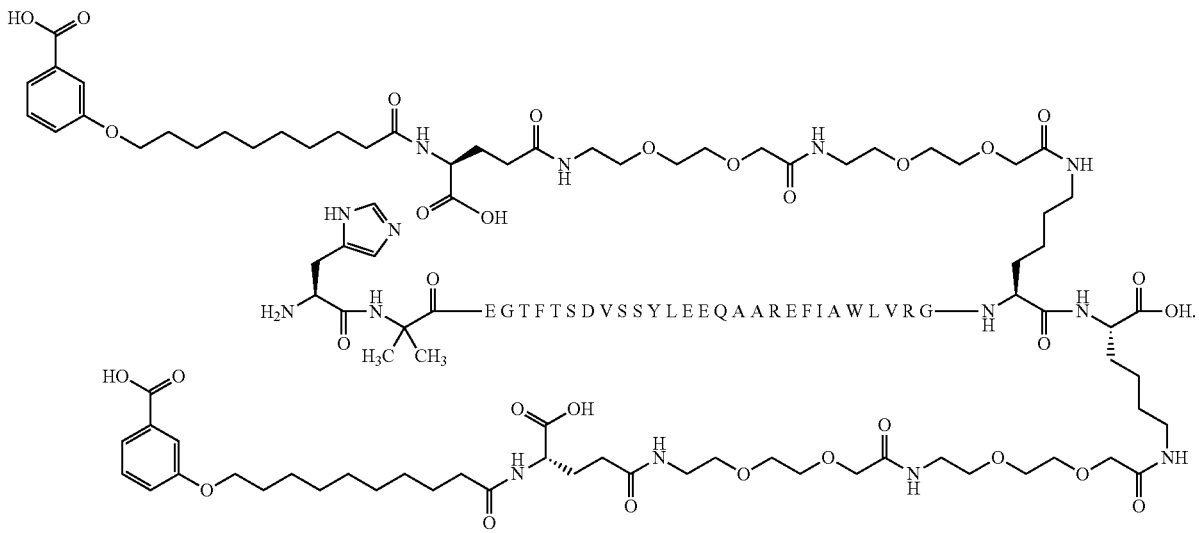

The amino acid sequence of compound E is set forth in SEQ ID NO: 10.

50. The pharmaceutical composition according to any one of the preceding embodiments, wherein said GLP-1 receptor agonist is selected from the group consisting of semaglutide, Compound A, Compound B, Compound C, Compound D, and Compound E.

51. The pharmaceutical composition according to any one of the preceding embodiments, wherein said GLP-1 receptor agonist is selected from the group consisting of semaglutide, Compound A, Compound B, and Compound E.

Excipients

52. The solid pharmaceutical composition according to any one of the preceding embodiments, wherein said solid pharmaceutical composition comprises one or more pharmaceutically acceptable excipients.

53. The solid pharmaceutical composition according to any one of the preceding embodiments, wherein said solid pharmaceutical composition comprises a filler, such as sorbitol.

54. The solid pharmaceutical composition according to any one of the preceding embodiments, wherein said solid pharmaceutical composition comprises a lubricant, such as stearic acid.

Product-by-Process: Enteric Coating

55. The solid pharmaceutical composition according to any one of the preceding embodiments, wherein said first coating is obtained from a dispersion comprising between 25-35% w/w, such as 30% w/w, methacrylate copolymer as defined in any one of the preceding embodiments.

Processes

56. A method for producing a solid pharmaceutical composition as defined in any one of the preceding embodiments, wherein said method comprises the steps of preparing a tablet core and applying a coating completely surrounding said tablet core, wherein said coating is an anionic copolymer coating obtained from a dispersion comprising between 25-35% w/w, such as 30% w/w, methacrylate copolymer as defined in any one of the preceding embodiments.

Method of Treatment

57. A solid pharmaceutical composition as defined in any one of the preceding embodiments for use as a medicament.

58. A solid pharmaceutical composition according to the preceding embodiment for use treatment or prevention of type 2 diabetes or obesity.

59. A method for treatment or prevention of type 2 diabetes or obesity comprising administering a solid pharmaceutical composition as defined in any one of the preceding embodiments.

EXAMPLES

Materials

Eudragit® FS 30 D, Eudragit® L 30 D-55, Eudragit® S 100, Plasacryl™ T20, and Plasacryl™ HTP20 were used as sold by Evonik Industries, Essen, Germany in 2014. Opadry® Clear 03K19229, Opadry® II Yellow 85F32410, Acryl-EZE® 93O18509, Acryl-EZE® 93A18597 and Opadry® White 03F180011 were used as sold by Colorcon, Pa., USA, 2014. Pharmacoat® 603 was used as sold by Shin-Etsu Ltd., Tokyo, Japan, in 2014. Kollicoat® IR was used as sold by BASF, Ludwigshafen, Germany, in 2014. GLP-1 agonists may be prepared according to methods known in the art. For example, semaglutide may be prepared as described in Example 4 of WO2006/097537. Compound A may be prepared as described in Example 2 of WO2011/080103. Compound B may be prepared as described in Example 31 of WO2012/140117.

Method 1: Tablet Core

The formulation of a tablet core material according to the present invention was performed as outlined here, this example concerns formulations of the present invention comprising:

| | |
|---|---|
| a) GLP-1 agonist | 1.41% w/w, |
| b) sodium caprate | 77.46% w/w, |
| c) sorbitol | 20.63% w/w, and |
| d) stearic acid | 0.50% w/w. |

When 100 g of tablet core material comprising GLP-1, sodium caprate, sorbitol and stearic acid was manufactured according to the above listed ingredients and in the corresponding ratios, the following steps were used:

The correct amount of GLP-1 was weighed. Sorbitol powder was sieved using a mesh size of 0.5 mm followed by weighing the correct amount of sorbitol.

GLP-1 and sorbitol were mixed in a small container. An amount of sorbitol equivalent to the amount of GLP-1 was added to the container and mixed by hand. Then the double amount of sorbitol relative to the previous addition was added and mixed by hand until GLP-1 and all sorbitol were mixed well. This step was followed by a mechanical mixing in a Turbula-mixer to finalize the mixing to obtain a homogeneous blend consisting of GLP-1 and sorbitol.

Sodium caprate (in the form of granulate) was then added to the blend consisting of GLP-1 and sorbitol according to the equal volumes principle. A granulate of sodium caprate may be prepared by granulation. This was done in two steps and finalized with a mechanical mixing step in a Turbula-mixer resulting in a blend consisting of GLP-1, sorbitol, and sodium caprate.

Finally, stearic acid was sieved using a mesh size of 0.3 mm followed by weighing of the correct amount of stearic acid, and addition hereof to the blend consisting of GLP-1, sorbitol, and sodium caprate and mixed mechanically resulting in the final granulate.

The final granulate was then compressed in a tablet press to form tablets of a mass of 710 mg, unless otherwise stated herein, via a standard tabletting process, for example using a Fette 102I tablet press. Tablets were produced to a technical level allowing for further processing such as e.g. coating.

Method 2a: Sub-Coat (Opadry® Clear 03K19229)

A tablet core prepared by Method 1 was coated with a sub-coat comprising Opadry® Clear 03K19229. The coating suspension was prepared by a) adding 6 g Opadry® Clear 03K19229 coating material (polymer powder) into 94 g demineralised water under intense mixing using a standard magnetic stirrer, following by b) stirring at low intensity for 45 minutes, and finally c) sieving the suspension to remove lumps. Coating of tablet cores was performed in a pan coater with the pan size of 8.5", with a conventional patterned air Schlick spray nozzle with an orifice of 1.0 mm, an atomizing and pattern air pressure of 0.55 bar, inlet air temperature of 40° C. and air flow of 100 kg/hour. After addition of the required amount of coating suspension (e.g. 1.5% w/w dry weight of the polymer powder) distributed evenly on the tablet cores the spraying was stopped and the tablets dried for up to 30 minutes inside the pan.

Method 2b: Sub-Coat (Opadry II Yellow 85F32410)

A tablet core prepared by Method 1 was coated with a sub-coat comprising Opadry II Yellow 85F32410. The coating suspension was prepared by a) adding 30 g Opadry II Yellow (polymer powder) into 120 g demineralised water under intense mixing using a standard magnetic stirrer, followed by b) stirring at low intensity for 45 minutes, and finally c) sieving to remove lumps. Coating of tablet cores was performed by the method described in Method 2a by using an inlet air temperature of 37° C. After addition of the required amount of coating suspension (e.g. 5.5% w/w dry weight of the Opadry II Yellow coating material) distributed evenly on the tablets the spraying was stopped and the tablets dried for up to 30 minutes inside the pan.

Method 2c: Sub-Coat (Pharmacoat® 603)

A tablet core prepared by Method 1 was coated with a sub-coat comprising Pharmacoat® 603. The coating suspension was prepared by a) wetting 10 g Pharmacoat® 603 with 90 g boiled water while stirring with a spoon b) dissolving 2 g triacetin in 112 g demineralised water and add it to the hypromellose suspension, following by c) stirring at low intensity for up to 45 min. Then d) adding 0.9 g Talc to the suspension, and finally e) homogenization the suspension for at least 15 min. Coating of tablet cores was performed according to Method 2a. After addition of the required amount of coating suspension (e.g. 1.5% w/w dry weight of the hypromellose coating material) distributed evenly on the tablets the spraying was stopped and the tablets dried for up to 30 minutes inside the pan.

Method 2d: Sub-Coat (Kollicoat® IR)

A tablet core prepared by Method 1 was coated with a sub-coat comprising Kollicoat® IR. The coating suspension was prepared by a) adding 15 g Kollicoat® IR (polymer powder) in 85 g demineralised water under intense mixing using a standard magnetic stirrer, following by b) stirring at low intensity for 45 minutes, and finally c) sieving the suspension to remove lumps. Coating of tablet cores was performed by the method described in Method 2a by using an inlet air temperature of 38° C. After addition of the required amount of coating suspension (e.g. 1.5% w/w dry weight of the Kollicoat® IR coating material) distributed evenly on the tablets the spraying was stopped and the tablets dried for up to 30 minutes inside the pan.

Method 3A: Anionic Copolymer Coated Tablet (Eudragit® FS 30 D)

An anionic copolymer coating was applied on i) a tablet core prepared according to Method 1 herein, or ii) a tablet core coated with a sub-coat prepared according to Method 1 and one of Methods 2a-d herein, according to the following method:

121.2 g of an aqueous dispersion of Eudragit® FS 30 D coating material was placed in a beaker on a suitable stirring apparatus. 18.2 g PlasAcryl™ T20 and 60.6 g demineralised water were mixed for 5 minutes and then added to the aqueous dispersion of FS30D coating material while stirring. The mixture was allowed to mix for 10 minutes prior to a filtration through a 0.24 mm mesh filter to remove lumps resulting in the coating suspension. Coating with the coating suspension was performed in a pan coater with the pan size of 8.5", with a conventional patterned air Schlick spray nozzle with an orifice of 1.0 mm, an atomizing and pattern air pressure of 0.5-0.7 bar, inlet air temperature of 36° C., air flow of 100 kg/hours. After addition of the required amount of coating suspension (e.g. 6.4% w/w dry weight of the Eudragit® FS 30 D coating material) distributed evenly on the tablets, the spraying was stopped and the tablets dried for up to 30 minutes inside the pan.

Method 3b: Anionic Copolymer Coated Tablet (combination of Eudragit® FS 30 D and Eudragit® L 30 D-55)

An anionic copolymer coating was applied on i) a tablet core prepared according to Method 1 herein, or ii) a tablet core coated with a sub-coat prepared according to Method 1 and one of Methods 2a-d herein, according to the following method: 17.4 g PlasAcryl™ T20 was mixed with 20.0 g demineralised water for 5 min while stirring. 1.7 g triethylcitrate was mixed with 44.9 g demineralised water for 5 min and then added to PlasAcryl™ T20. 92.8 g of an aqueous dispersion of Eudragit® FS 30 D coating material was placed in a beaker on a suitable stirring apparatus. The PlasAcryl™ T20 suspension and 23.2 g L30D-55 coating material were added to the FS30D suspension while stirring for at least 10 min prior to filtration through a 0.24 mm mesh filter to remove lumps resulting in the coating suspension. The amounts of Eudragit® FS 30 D and Eudragit® L 30 D-55 described here results in a 80:20 ratio between Eudragit® FS 30 D and Eudragit® L 30 D-55 and may be adjusted to allow other ratios, such as 50:50 for which 58 g of each of the Eudragit® FS 30 D and Eudragit® L 30 D-55 coating materials may be weighed. Coating was performed according to Method 3a with an inlet air temperature of 37° C. After addition of the required amount of coating suspension (e.g. 6.4% w/w dry weight of the combination of Eudragit® FS 30 D and Eudragit® L 30 D-55 coating materials) distributed evenly on the tablets, the spraying was stopped and the tablets dried for up to 30 minutes inside the pan.

Method 3c: Anionic Copolymer Coated Tablet (Eudragit® S 100)

An anionic copolymer coating was applied on i) a tablet core prepared according to Method 1 herein, or ii) a tablet core coated with a sub-coat prepared according to Method 1 and one of Methods 2a-d herein, according to the following method: 324 g of isopropanol was mixed with 36 g of demineralised water. 25 g Eudragit® S 100 (polymer powder) was dispersed into half of the isopropanol:water diluent under intense mixing using a standard magnetic stirrer. After addition of the polymer powder the mixture was stirred at low intensity for up to 60 minutes to form a coating solution. 12.5 g talc, 2.5 g triethyl citrate and the remaining isopropanol:water diluent was homogenized for at least 10 min. This suspension was added slowly to the coating solution while stirring and then sieved to remove lumps.

Coating was performed according to Method 3a with an inlet air temperature of 32° C. After addition of the required amount of coating suspension (e.g. 4.5% w/w dry weight of Eudragit® S 100 coating material) distributed evenly on the tablets, the spraying was stopped and the tablets dried for up to 30 minutes inside the pan.

Method 3d: Anionic Copolymer Coated Tablet (Acryl-EZE® 93O18509/93A18597)

An anionic copolymer coating was applied on i) a tablet core prepared according to Method 1 herein, or ii) a tablet core coated with a sub-coat prepared according to Method 1 and one of Methods 2a-d herein, according to the following method:

4 g of triethyl citrate was dispersed into 156 g of demineralised water under stirring for 5 min. 40 g Acryl-EZE® with the product number 93O18509 or 93A18597 (polymer powder) was added under intense mixing using a standard magnetic stirrer. After addition of the polymer powder the coating suspension was stirred at low intensity for 45 minutes. The coating suspension was sieved to remove lumps. Coating was performed according to the Method 3a with an inlet air temperature of 36° C. After addition of the required amount of coating suspension e.g. 9.2% w/w dry weight of the Acryl-EZE® coating distributed evenly on the tablets the spraying was stopped and the tablets dried for up to 30 minutes inside the pan.

Method 4A: Top-Coat (Opadry® White 03F180011)

Coating with a top-coat consisting of Opadry White was applied to a coated tablet obtained according to i) Method 1, one of Methods 2a-d, and one of Methods 3a-d (i.e. tablet core with sub-coat and further coating, e.g. anionic copolymer coating), or ii) Method 1 and one of Methods 3a-d (i.e. tablet core without sub-coat and with a single coating, e.g. anionic copolymer coating). The coating suspension was prepared by a) adding 15 g Opadry® White 03F180011 coating material into 135 g demineralised water under intense mixing using a standard magnetic stirrer, following by b) stirring at low intensity for 45 minutes, and finally c) sieving the suspension to remove lumps. The coating of tablet cores was performed in a pan coater. In a pan coater with a pan size of 8.5", and with a conventional patterned air Schlick spray nozzle having an orifice of 1.0 mm, an atomizing and pattern air pressure of 0.5-0.7 bar, inlet air temperature of 36-37° C. and air flow of 100 kg/hour. After addition of the required amount of coating suspension (e.g. 2.4% w/w dry weight of the Opadry® White 03F180011 coating material) distributed evenly on the tablets, the spraying was stopped and the tablets were dried for up to 30 minutes inside the pan.

Method 4b: Top-Coat (Opadry® II Yellow 83F32410)

Coating with an top-coat consisting of Opadry II Yellow was performed using a coated tablet obtained according to i) Method 1, one of Methods 2a-d, and one of Methods 3a-d (i.e. tablet core with sub-coat and further coating, e.g. anionic copolymer coating), or ii) Method 1 and one of Methods 3a-d (i.e. tablet core without sub-coat and with a single coating, e.g. anionic copolymer coating). Preparation of the coating suspension and coating of tablets were performed according to Method 2b. After addition of the required amount of coating suspension e.g. 2.5% w/w dry weight of the Opadry® II Yellow 83F32410 distributed evenly on the tablets the spraying was stopped and the tablets dried for up to 30 minutes inside the pan.

Method 4c: Top-Coat (Eudragit® L 30 D-55)

Coating with an top-coat consisting of L30D-55 was performed using a coated tablet obtained according to i) Method 1, one of Methods 2a-d, and one of Methods 3a-d (i.e. tablet core with sub-coat and further coating, e.g. anionic copolymer coating), or ii) Method 1 and one of Methods 3a-d (i.e. tablet core without sub-coat and with a single coating, e.g. anionic copolymer coating).

The coating suspension was prepared by a) mixing 29.1 g PlasAcryl™ HTP20 with 57 g demineralised water for 5 min while stirring b) adding 114 g of an aqueous dispersion of Eudragit® L 30 D-55 into the mixture under stirring for at least 10 min, and finally c) sieving the suspension to remove lumps.

Application of the coating was performed according to Method 4a. After addition of the required amount of coating suspension (e.g. 0.9% w/w dry weight of Eudragit® L 30 D-55 coating material) distributed on the tablets, the spraying was stopped and the tablets dried for up to 30 minutes inside the pan.

Method 5: Solubility pH of the Coating

Solubility of coated tablets according to the present invention comprising a tablet core coated with i) sub-coat and further coating, e.g. anionic copolymer coating), or with ii) a single coating, e.g. anionic copolymer coating were tested at various pH values. Tablets were placed in beakers under the pH conditions specified herein. After treatment the individual tablets were weighed. The weight was recorded as positive if the tablet increased in weight or negative if the tablet lost weight relative to the initial weight. Initially tablets were subjected to 0.1N HCl adjusted to pH 1.2 for two periods of 1h each. The pH was increased to pH 4.5 with mixtures of 1M $NaH_2PO_4$ and 0.5M $NaH_2PO_4$ and the tablets were kept at this set point pH for 30 minutes. This was repeated in pH 5.5, 6.0, 6.5, 7 and 7.4 and the weight loss/weight gain was recorded for all pH values.

Method 6: Dissolution Rate In Vitro

In an appropriate dissolution apparatus e.g. USP dissolution apparatus 2 a standard dissolution test according to the pharmacopoeia (Ph Eur 2.9.3) may be performed to measure dissolution in-vitro. In the present invention the test was carried out at 37° C.±0.5° C. Initially, dissolution was performed in 500 ml, 0.1N HCl, pH 1.2 for 120 minutes. Then 400 ml 0.12M phosphate solution containing 0.225% BRIJ 35 was added to neutralize the acid and bring pH to 7.4. Hereafter, dissolution was further followed for 120 min. Samples were collected at given time points and quantified for GLP-1 as well as sodium caprate by HPLC chromatography.

Method 7: In Vivo Studies in Beagle Dogs

The day before the experiment the Beagle dogs were weighed and fed their normal diet at 12 pm and was given an overnight fast with ad libitum access to water. On the day of the experiment the dogs were placed on a test platform and fitted with a 20G Venflon in v. cephalica to allow for blood sampling. During the first 2.5-4h the blood samples were collected from the Venflon after which time the Venflon was removed and the dogs returned to their pens. For subsequent blood sampling the dogs were lead into a test room and a blood sample was taken from the v. jugularis using a standard 21G needle and a syringe. This procedure was also employed when it was not possible to place a venflon in v. cephalica. In a subset of studies the dogs remained in their pens also in the first 4 h and were lead to a test room were all blood samples were taken from the v. jugularis using a standard 21G needle and a syringe. The dogs were fed 4 h after dosing.

a) Oral Administration of Tablets after Subcutaneous Pentagastrin Injection:

The dogs were positioned on the test platform and after placement of the venflon then the tablet was administered in the following manner: Acid secretion was induced before administration of the oral tablet by subcutaneous administration in the neck of pentagastrin at a dose of 4 µg/kg body weight (120 µg/mL) 20 minutes prior to oral administration of the tablet. The tablet was placed in the back of the mouth of the dog in order to prevent chewing. The mouth was closed and 10 mL of tap water was given by a syringe to facilitate swallowing of the tablet. In some studies the dogs were not on platforms but were dosed when they were still in the pens.

b) Intravenous Dosing:

The dogs were positioned on the test platform and after placement of the venflon in v. cephalica the GLP-1 agonist was administered intravenously in v. cephalica of the other front leg by using a 23G butterfly needle. After the GLP-1 agonist was administered the bufferfly was flushed using physiological saline containing 10 IU/mL of heparin. In some studies, dogs were not on platforms and fitted with a venflon but remained in their pens and were dosed directly into the v. cephalica.

Blood Sampling:

The following applies to all types of studies described in the current invention. Before each blood sampled was collected the first few drops were allowed to drain from the venflon to avoid saline from the venflon in the sample. For each time point ~800 µL of whole blood was collected in a 1.5 mL EDTA coated tube, and the tube was gently turned to allowing mixing of the sample and the anticoagulant. The samples were placed on wet ice until centrifugation at 4000G (4° C.) for 4 min, and afterwards pipetted on dry ice into micronic tubes for later analysis of GLP-1 agonist. All samples were kept on −80° C. until plasma analysis. Blood samples were collected to adequately cover the full plasma concentration-time profile of the GLP-1 agonist. For example blood samples may be collected at t=predose, 0.25, 0.5, 0.75, 1, 1.5, 2, 4, 6, 8, 10, 24, 48, 72, 120, 144, 168, 192, 216, 240, 288 h after dose. After each blood sample the Venflon was flushed using 0.5 mL saline containing heparin (10 IU/mL). All plasma samples were analyzed using either sandwich immunoassay (LOCI) or Liquid chromatography-mass spectrometry.

given a light meal of Hills I/D, an easily absorbable canned diet. 30 minutes following the diet the tablet was administered, the position of the diet and the tablet was confirmed with ultrasound. After administration of the tablet a standard blood sampling regimen was performed according to the protocol described in Method 7 herein.

Example 1

In a first study tablet cores were prepared by mixing the ingredients listed in Table 1 according to Method 1 and coated according to Method 2a, 3a and 4a resulting in tablets comprising a tablet core, an Opadry Clear sub-coat an FS30D enteric coating and an Opadry White top-coat. The amount of GLP-1 agonist was 10 mg.

Table 1 shows the composition of the tablet of Example 1. The tablet comprised a GLP-1 agonist in the tablet core which also comprised sodium caprate and the tablet core was coated with Opadry Clear, FS30D and Opadry White. Specifically, the tablet core consisted of GLP-1 agonist, sodium caprate, sorbitol, and stearic acid. The tablet core weight was 710 mg, the enteric coated tablet with sub-coat and top-coat weight was 790.4 mg.

TABLE 1

| Tablet Excipient | Amount per tablet (mg) | Concentration in tablet core (% w/w) | Concentration in final coated tablet (% w/w) | Location in the tablet | Function |
|---|---|---|---|---|---|
| Compound A | 10 | 1.4 | 1.3 | Tablet core | GLP-1 agonist |
| Sodium caprate | 550 | 77.5 | 69.6 | Tablet core | Permeation enhancer |
| Parteck SI 150 (Sorbitol) | 146.4 | 20.6 | 18.5 | Tablet core | Filler |
| Stearic Acid | 3.6 | 0.5 | 0.5 | Tablet core | Lubricant |
| Opadry Clear | 10.7 | N/A | 1.4 | Second coating | Sub-coat |
| FS30D | 50.4 | N/A | 6.4 | First coating | Enteric coat |
| Opadry White | 19.3 | N/A | 2.4 | Third coating | Top-coat |

Method 8: Oral Bioavailability in Dogs

Increased oral bioavailability of a drug substance means that a larger fraction of the drug substance administered orally reaches the systemic circulation from where it can distribute to exhibit pharmacological effect. Generally, the term bioavailability refers to the fraction of an administered dose of a drug substance that reaches the systemic circulation unchanged. By definition, when a drug substance is administered intravenously its bioavailability is 100%. However, the drug substance can be incompletely absorbed following oral administration, or be degraded either within the intestinal lumen or in first pass hepatic metabolism.

A plasma concentration-time plot was made and using NCA the dose-corrected AUC was calculated after both oral administration and intravenous administration to beagle dogs performed as described in Method 7 herein, specifically absolute bioavailability (F) was calculated as $AUC/D_{po}$ divided by $AUC/D_{iv}$.

Method 9: Food Interaction

Food interaction was evaluated when the tablet was administered orally after feeding. The presence of food within the stomach may interfere with the performance of a tablet administered orally possibly resulting in decreased oral bioavailability of a drug substance. This experiment was carried out as described in Method 7a herein with the following modifications: The dogs were fasted overnight, and not provided with water from 7-8 am at the day of testing. At 8 am the stomach of the dogs was ultrasound scanned to ensure an empty stomach. The dogs were then Example 2

In another study tablets were prepared as described in Example 1; wherein tablet cores prepared according to Method 1 were scaled down to ⅓; wherein tablets were coated according to Method 2a, 3a and 4a based on surface area calculation to obtain the same coating thickness as for the tablets in Example 1; and wherein the tablets had the following specifications:
GLP-1 agonist: Compound A
Sub-coat: 2.2% w/w Opadry Clear
Enteric coat: 10.2% w/w FS30D
Top-coat: 3.7% w/w Opadry White Example 3

In another study tablets were prepared as described in Example 1; wherein the tablets were coated with the combination of FS30D and L30D-55 in the ratio 80:20; wherein tablets were coated according to Method 2a, 3b and 4a; and with the following specifications:
GLP-1 agonist: Compound A
Sub-coat: 1.5% w/w Opadry Clear
Enteric coat: 7% w/w 80:20 FS30D:L30D-55
Top-coat: 2.5% w/w Opadry White Example 4 (Reference)

In another study tablets were prepared as described in Example 1; wherein tablets were coated with a PVA sub-coat and Methacrylic acid copolymer type C and without top-coat; wherein tablets were coated according to Method 2b and 3d; and with the following specifications:
GLP-1 agonist: Compound A
Sub-coat: 4.5% w/w Opadry II Yellow
Enteric coat: 11.6% w/w Acryl-EZE 93A Example 5

In another study tablets were prepared as described in Example 1; wherein tablets were coated without sub-coat, without top-coat and with the combination of FS30D and L30D-55 in the ratio of 50:50; wherein tablets were coated according to Method 3b; and with the following specifications:
GLP-1 agonist: Compound A
Enteric coat: 7% w/w 50:50 FS30D:L30D-55

Example 6

In another study tablets were prepared as described in Example 1; wherein tablets were coated without sub-coat and with the combination of FS30D and L30D-55 in the ratio of 80:20; wherein tablets were coated according to Method 3b; and with the following specifications:
GLP-1 agonist: Compound A
Enteric coat: 7% w/w 80:20 FS30D:L30D-55

Example 7

In another study tablets were prepared as described in Example 1; wherein tablets were coated with the sub-coat Pharmacoat and with the enteric coat S100; wherein tablets were coated according to Method 2c and 3c; and with the following specifications:
GLP-1 agonist: Compound A
Sub-coat: 1.5% w/w Pharmacoat
Enteric coat: 4.5% w/w S100

Example 8

In another study tablets were prepared as described in Example 1; wherein tablets were coated without sub-coat; wherein tablets were coated according to Method 3a and 4a; and with the following specifications:
GLP-1 agonist: Compound A
Enteric coat: 7% w/w FS30D
Top-coat: 2.5% w/w Opadry White Example 9

In another study tablets were prepared as described in Example 1; wherein tablets were coated with 3% w/w sub-coat and the combination of FS30D:L30D-55; wherein tablets were coated according to Method 2c and 3b; and with the following specifications:
GLP-1 agonist: Compound A
Sub-coat: 3% w/w Pharmacoat
Enteric coat: 7% w/w 80:20 FS30D:L30D-55

Example 10

In another study tablets were prepared as described in Example 1; wherein tablets were coated with 3% w/w sub-coat and FS30D; wherein tablets were coated according to Method 2c and 3a; and with the following specifications:
GLP-1 agonist: Compound A
Sub-coat: 3% w/w Pharmacoat
Enteric coat: 7% w/w FS30D Example 11

In another study tablets were prepared as described in Example 1; wherein tablets were coated with a PVA-PEG sub-coat; wherein tablets were coated according to Method 2d and 3b; and with the following specifications:
GLP-1 agonist: Compound A
Sub-coat: 1.5% w/w Kollicoat
Enteric coat: 7% w/w 80:20 FS30D:L30D-55

Example 12

In another study tablets were prepared as described in Example 1; wherein tablets were coated with 6% w/w of the combination coating FS30D:L30D-55 80:20; wherein tablets were coated according to Method 2c and 3b; and with the following specifications:
GLP-1 agonist: Compound A
Sub-coat: 1.5% w/w Pharmacoat
Enteric coat: 6% w/w 80:20 FS30D:L30D-55

Example 13

In another study tablets were prepared as described in Example 1; wherein tablets were coated with 8% w/w of the combination coating FS30D:L30D-55 80:20; wherein tablets were coated according to Method 2c and 3b; and with the following specifications:
GLP-1 agonist: Compound A
Sub-coat: 1.5% w/w Pharmacoat
Enteric coat: 8% w/w 80:20 FS30D:L30D-55

Example 14

In another study tablets were prepared as described in Example 1; wherein tablets were coated with 10% w/w of the combination coating FS30D:L30D-55 80:20; wherein tablets were coated according to Method 2c and 3b; and with the following specifications:
GLP-1 agonist: Compound A
Sub-coat: 1.5% w/w Pharmacoat
Enteric coat: 10% w/w 80:20 FS30D:L30D-55

Example 15

In another study tablets were prepared as described in Example 1; wherein tablets were coated with a PVA top-coat; wherein tablets were coated according to Method 2a, 3a and 4b; and with the following specifications:
GLP-1 agonist: Compound A
Sub-coat: 1.5% w/w Opadry Clear
Enteric coat: 7% w/w FS30D
Top-coat: 2.5% w/w Opadry II Yellow Example 16

In another study tablets were prepared as described in Example 1; wherein tablets were coated with a L30D-55 top-coat; wherein tablets were coated according to Method 2a, 3a and 4c; and with the following specifications:
GLP-1 agonist: Compound A
Sub-coat: 1.5% w/w Opadry Clear
Enteric coat: 6% w/w FS30D
Top-coat: 1% w/w L30D-55

Example 17

In another study tablets were prepared as described in Example 1; wherein semaglutide was used as GLP-1 agonist and no sub-coat or top-coat was applied; wherein tablets were coated according to Method 3a; and with the following specifications:
GLP-1: Semaglutide
Enteric coat: 7% w/w FS30D

Example 18

In another study tablets were prepared as described in Example 1; wherein Compound B was used as GLP-1 agonist; wherein tablets were coated according to Method 2a, 3a and 4a; and with the following specifications:
GLP-1 agonist: Compound B
Sub-coat: 1.5% w/w Opadry Clear
Enteric coat: 7% w/w FS30D
Top-coat: 2.5% w/w Opadry White

Example 19

In another study tablets were prepared as described in Example 1; wherein no sub-coat or top-coat was applied; wherein tablets were coated according to Method 3a; and with the following specifications:
GLP-1 agonist: 5 mg Compound B
Enteric coat: 7% w/w FS30D

Example 20

In another study tablets were prepared as described in Example 1; wherein the combination coating FS30D:L30D-55 80:20 was applied and no top-coat; wherein tablets were coated according to Method 2c and 3b; and with the following specifications:
GLP-1 agonist: 5 mg Compound B
Sub-coat: 1.5% w/w Pharmacoat
Enteric coat: 7% w/w 80:20 FS30D:L30D-55

Example 21

In another study tablets were prepared as described in Example 1; wherein tablets were coated according to Method 2a, 3a and 4a; and with the following specifications:
GLP-1 agonist: Semaglutide
Sub-coat: 1.5% w/w Opadry Clear
Enteric coat: 7% w/w FS30D
Top-coat: 2.5% w/w Opadry White

Example 22 (Reference)

In one study tablets were prepared as described in Example 1; wherein tablets were coated according to Method 2b and 3d; and with the following specifications:
GLP-1 agonist: Compound A
Sub-coat: 5.6% w/w Opadry II Yellow
Enteric coat: 9.2% w/w Acryl-EZE 93O

Example 23

In another study tablets were prepared as described in Example 1; wherein tablets were coated according to Method 2c and 3a; and with the following specifications:
GLP-1 agonist: Compound A
Sub-coat: 1.5% w/w Pharmacoat
Enteric coat: 7% w/w FS30D

Example 24

In another study tablets were prepared as described in Example 1; wherein tablets were coated according to Method 2c and 3b; and with the following specifications:
GLP-1 agonist: Compound A
Sub-coat: 1.5% w/w Pharmacoat
Enteric coat: 7% w/w 80:20 FS30D:L30D-55

Example 25

In another study tablets were prepared as described in Example 1; wherein semaglutide tablets were coated with FS30D and tested in-vivo after storage at 5° C. for 2, 8 and 15 weeks after manufacturing was completed; wherein tablets were coated according to Method 2c and 3a; and with the following specifications:
GLP-1 agonist: Semaglutide
Sub-coat: 1.5% w/w Pharmacoat
Enteric coat: 7% w/w FS30D

Example 26

In another study tablets were prepared as described in Example 1; wherein tablets were coated according to Method 2c and 3b; and with the following specifications:
GLP-1 agonist: Semaglutide
Sub-coat: 1.5% w/w Pharmacoat
Enteric coat: 7% w/w 80:20 FS30D:L30D-55

Example 27

In another study tablets were prepared as described in Example 1; wherein tablets were coated according to Method 2a, 3b and 4a; and with the following specifications:
GLP-1 agonist: Semaglutide
Sub-coat: 1.5% w/w Opadry Clear
Enteric coat: 7% w/w 80:20 FS30D:L30D-55
Top-coat: 2.5% w/w Opadry White

Example 28

In another study tablets were prepared as described in Example 1; wherein tablets were coated according to Method 2c and 3b; and with the following specifications:
GLP-1 agonist: Compound C
Sub-coat: 1.5% w/w Pharmacoat
Enteric coat: 7% w/w 80:20 FS30D:L30D-55

Example 29

In another study tablets were prepared as described in Example 1; wherein tablets were coated according to Method 2a and 3b; and with the following specifications:
GLP-1 agonist: Compound D
Sub-coat: 1.5% w/w Opadry Clear
Enteric coat: 7% w/w 80:20 FS30D:L30D-55

The weight of the final coating as applied in Examples 2-29 may be determined in relation to weight of the unit onto which the coating is applied (e.g. in Example 2 the amount of sub-coat applied may be 2.2% w/w of the tablet unit consisting of a tablet core; similarly, the amount of top-coat applied may be 3.7% w/w of the tablet unit consisting of a tablet core, a sub-coat and an enteric coat).

Example 30—pH Dependency of Coating

Coated tablets from Example 4, 6, 8, 22, 23 and 24 were tested according to Method 5. The results are shown in Table 2 and are presented as percent weight gain of enteric coated tablets exposed to different pH conditions. Weight gain indicates the hydration of the given enteric coating as a function of pH. The results show that, as pH increases weight gain was seen in all cases. Once the coating reaches its maximum limit pH for enteric protection, the tablets starts to dissolve.

TABLE 2

| Example | Weight gain (% w/w) | | | | | | | |
|---|---|---|---|---|---|---|---|---|
| | pH 1.2 (1 hr) | pH 1.2 (2 hr) | pH 4.5 | pH 5.5 | pH 6.0 | pH 6.5 | pH 7.0 | pH 7.4 |
| 8 | 0.8 | 1.6 | 1.9 | 2.3 | 3.0 | 3.9 | 15.0 | Dissolved** |
| 23 | 0.6 | 1.1 | 1.1 | 1.3 | 1.4 | 1.6 | 8.8 | Dissolved |
| 6 | 0.7 | 1.4 | 1.6 | 2.0 | 10.6 | 25.1 | 24.6 | Dissolved |
| 24 | 0.7 | 1.2 | 1.4 | 1.6 | 7.1 | 21.0 | 40.4 | Dissolved |
| 4* | — | 2.8 | 3.5 | Dissolved | | | | |
| 22* | 1.7 | 3.1 | Dissolved | | | | | |

*Reference examples comprising coatings which are not part of the present invention.
**The term "Dissolved" refers to that the coating is at least partly dissolved and that the total tablet weight is less than before the start of the experiment.

The data in Table 2 show that the combination coating FS30D:L30D 80:20 could take up much more water than the FS30D at pH 6.0, 6.5, and 7.0 due to the solubility of L30D-55 at pH 5.5; however, both coatings dissolved at pH 7.4. In contrast, the Acryl-EZE 93A coating dissolved already at pH 5.5 and the Acryl-EZE 93O coating dissolved at pH 4.5. The combination FS30D:L30D-55 80:20 and the pure FS30D coating gives a much better protection of the core if the stomach pH increases to neutral compared to the Acryl-EZE coatings.

Example 31—Dissolution Rate

Dissolution was performed according to Method 6. Table 3 shows the results for tablets prepared according to the present invention, wherein dissolution is presented as "GLP-1 in solution (%)" which refers to the amount of GLP-1 in solution after 15 min, 30 min and 60 min relative to the total amount of GLP-1 in the tablet at the start of the experiment.

TABLE 3

| Example | GLP-1 in solution (%) | | |
|---|---|---|---|
| | 15 min | 30 min | 60 min |
| 1 | 11.2 | 38.0 | 99.1 |
| 2 | 4.1 | 10.9 | 86.1 |
| 3 | 2.2 | 16.7 | 82.0 |
| 4 | 7.7 | 52.8 | 94.0 |
| 5 | 8.1 | 56.8 | 92.4 |
| 6 | 6.7 | 41.9 | 95.0 |
| 7 | 12.6 | 45.6 | 97.5 |
| 8 | 12.9 | 65.3 | 100.4 |
| 9 | 0.0 | 10.9 | 80.0 |
| 10 | 0.6 | 12.8 | 84.7 |
| 11 | 5.7 | 35.9 | 84.9 |
| 12 | 4.5 | 39.6 | 97.9 |
| 13 | 1.2 | 14.3 | 81.9 |
| 14 | 1.0 | 5.2 | 49.0 |
| 15 | 1.7 | 17.9 | 93.3 |
| 16 | 1.3 | 16.0 | 84.8 |
| 17 | 13.5 | 61.1 | 98.3 |
| 18 | 1.5 | 9.6 | 79.5 |
| 19 | 13.1 | 55.9 | 96.7 |
| 21 | 6.2 | 30.2 | 93.9 |
| 22 | 15 | 75 | 89 |
| 23 | 3.7 | 29.1 | 94.5 |
| 24 | 3.1 | 24.1 | 88.0 |
| 25 | 3.6 | 36.2 | 98.0 |
| 26 | 2.6 | 24.1 | 92.9 |
| 27 | 0.5 | 12.1 | 80.8 |

The results in Table 3 show: All tablet Examples showed a prolonged release profile. The release was faster when no sub-coat was applied and slower when more sub-coat was applied. The fastest release was seen for the Acryl-EZE coated tablets. The amount of enteric coat impacted the release. Less enteric coat gave a faster release and more enteric coat gave a slower release. The different types of top-coat gave the same release profile and all GLP-1 agonists released the same way.

In another study dissolution was performed according to Method 6 but the phosphate buffer was changed to pH 6.5 and 5.5. These tests were performed for up to 3 hours and the results are given in Table 4, wherein dissolution is presented as "GLP-1 in solution (%)" which refers to the amount of GLP-1 in solution after 30 min, 60 min, 120 min and 180 min relative to the total amount of GLP-1 in the tablet at the start of the experiment.

TABLE 4

| Example | pH | GLP-1 in solution (%) | | | |
|---|---|---|---|---|---|
| | | 30 min | 60 min | 120 min | 180 min |
| 21 | 7.4 | 30.2 | 93.9 | 100.9 | — |
| 21 | 6.5 | 0 | 3.4 | 25.8 | 68.9 |
| 21 | 5.5 | 0.2 | 0.7 | 2.9 | 7.4 |
| 27 | 7.4 | 12.1 | 80.8 | — | — |
| 27 | 6.5 | 1.1 | 12.3 | 47.4 | 96.7 |
| 27 | 5.5 | 0.2 | 0.5 | 1.7 | 4.1 |

The results in Table 4 show: The release was much slower when pH was decreased below the pH at which the FS30D coating is soluble. The combination coating released more at pH 6.5 compared to the pure FS30D coating due to the solubility of L30D-55 above pH 5.5. Both formulations released very little in pH 5.5.

Example 32—Oral Bioavailability of GLP-1 Agonists

Oral bioavailability of GLP-1 agonists from tablets prepared according to the present invention was assessed according to Method 8 herein. The results are shown in Table 5.

TABLE 5

| Example | Oral bioavailability (%) |
|---|---|
| 1 | 2.7 |
| 2 | 1.3 |
| 3 | 2.8 |
| 4 | 0.4 |
| 5 | 1.6 |
| 6 | 2.9 |
| 7 | 2.9 |
| 8 | 2.9 (average of 3.2 and 2.5) |
| 9 | 3.4 |
| 10 | 2.0 |
| 11 | 3.0 |
| 12 | 3.4 |
| 13 | 2.8 |
| 14 | 1.3 |
| 15 | 2.7 |
| 16 | 2.7 |
| 17 | 0.7 |
| 18 | 3.5 |
| 19 | 4.4 |
| 20 | 2.9 |
| 28 | 2.4 |
| 29 | 3.4 |

The results in Tablet 5 show:

When the Acryl-EZE coated tablets were tested in dogs pre-treated with pentagastrin, to ensure an acidic pH in the stomach, the oral bioavailability was quite low (0.4%, Example 4) compared to FS30D coated tablets (2.7%, Example 1). As shown in Example 30, Acryl-EZE dissolves at pH 5.5. When the FS30D:L30D-55 50:50 enteric coating was tested the oral bioavailability of the GLP-1 agonist was not as high as for that of the FS30D:L30D-55 80:20 enteric coating indicating that a higher pH limit for solubility of the coating is beneficial.

The different GLP-1 agonists showed different oral bioavailability.

The oral bioavailability of the FS30D coated tablets was similar to the FS30D:L30D-55 80:20 coated tablets and similar to the organic S100 coated tablets. No difference in oral bioavailability was seen when applying different topcoats. When the amount of enteric coat was increased to 10% the oral bioavailability decreased. Tablets with and without sub-coat gave similar oral bioavailability.

Example 33—Food Interaction

Food interaction with the uptake of GLP-1 agonists was tested according to Method 9 herein. The results are given in Table 6 and are presented as the oral bioavailability of the GLP-1 agonist.

TABLE 6

| Example | Oral bioavailability (%) |
|---|---|
| 21 | 0.3 |
| 3 | 0.95 |
|  | 0.5 |
| 1 | 0.5 |

The results show that for Compound A the oral bioavailability decreased from 2.8% without food (see Table 5, Example 3) to an average of 0.7% when food was given 30 min prior to dosing while when food was given at the same time as the tablet then the oral bioavailability decreased to 0.5% (Example 1).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A solid pharmaceutical composition comprising
   i) a core comprising a salt of a medium-chain fatty acid and a GLP-1 agonist; and
   ii) a first coating consisting of an anionic copolymer coating, wherein the first coating which dissolves at pH 6.5 or higher,
   wherein said anionic copolymer coating comprises methacrylate copolymer, and wherein said methacrylate copolymer comprises
   a) 10-30% w/w methyl methacrylate,
   b) 50-70% w/w methyl acrylate, and
   c) 5-15% w/w methacrylic acid,
   and wherein the bioavailability of the GLP-1 agonist is improved as compared to a first coating which dissolves at less than pH 6.5.

2. The solid pharmaceutical composition according to claim 1, wherein said first coating is an enteric coating.

3. The solid pharmaceutical composition according to claim 1, wherein said composition does not comprise a protease inhibitor.

4. The solid pharmaceutical composition according to claim 1, wherein said first coating dissolves or at pH 7.0 or higher.

5. The solid pharmaceutical composition according to claim 1, wherein said solid pharmaceutical composition is in the form of a tablet.

6. The solid pharmaceutical composition according to claim 1, wherein said salt of a medium-chain fatty acid is a salt of a saturated fatty acid consisting of 6-14 carbon atoms.

7. The solid pharmaceutical composition according to claim 1, wherein said GLP-1 agonist is human GLP-1, exendin-4 or an analogue or derivative thereof.

8. The solid pharmaceutical composition according to claim 1, wherein said GLP-1 agonist is a GLP-1 analogue comprising Formula I:

Xaa7-Xaa8-Glu-Gly-Thr-Xaa12-Thr-Ser-Asp-Xaa16-
Ser-Xaa18-Xaa19-Xaa20-Glu-Xaa22-Xaa23-
Xaa24-Xaa25-Xaa26-Lys-Phe-Ile-Xaa30-Xaa31-
Leu-Val-Xaa34-Xaa35-Xaa36-Xaa37-Xaa38-
Xaa39 (SEQ ID NO: 4), wherein        Formula I:

Xaa7 is L-histidine, imidazopropionyl, α-hydroxy-histidine, D-histidine, desamino-histidine, 2-amino-histidine, β-hydroxy-histidine, homohistidine, Nα-acetyl-histidine, Nα-formyl-histidine, α-fluoromethyl-histidine, α-methyl-histidine, 3-pyridylalanine, 2-pyridylalanine, or 4-pyridylalanine;

Xaa8 is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa12 is Lys or Phe;
Xaa16 is Val or Leu;
Xaa18 is Ser, Arg, Asn, Gln, or Glu;
Xaa19 is Tyr or Gln;
Xaa20 is Leu, Lys, or Met;
Xaa22 is Gly, Glu, Lys, or Aib;
Xaa23 is Gln, Glu, or Arg;
Xaa24 is Ala or Lys;
Xaa25 is Ala or Val;
Xaa26 is Val, His, Lys or Arg;
Xaa30 is Ala, Glu, or Arg;
Xaa31 is Trp or His;
Xaa34 is Glu, Asn, Gly, Gln, or Arg;
Xaa35 is Gly, Aib, or absent;
Xaa36 is Arg, Gly, Lys, or absent;
Xaa37 is Gly, Ala, Glu, Pro, Lys, Arg, or absent;
Xaa38 is Ser, Gly, Ala, Glu, Gln, Pro, Arg, or absent; and
Xaa39 is Gly or absent.

9. The solid pharmaceutical composition according to claim 1, wherein said first coating is obtained from a dispersion comprising between 25-35% w/w-methacrylate copolymer.

10. A method for producing a solid pharmaceutical composition of claim 1, wherein said method comprises the steps of preparing a tablet core and applying a coating completely surrounding said tablet core, wherein said coating is an anionic copolymer coating obtained from a dispersion comprising between 25-35% w/w methacrylate copolymer.

11. The solid pharmaceutical composition according to claim 6, wherein said salt of a medium-chain fatty acid is a salt of capric acid.

12. The solid pharmaceutical composition according to claim 6, wherein said salt of a medium-chain fatty acid is sodium caprate.

13. The solid pharmaceutical composition according claim 1, wherein said GLP-1 agonist is selected from the group consisting of semaglutide, Compound A, Compound B, Compound C, Compound D, and Compound E.

14. A method of treating or preventing type 2 diabetes or obesity comprising administering to a patient in need thereof a solid pharmaceutical composition of claim 1.

15. The solid pharmaceutical composition according claim 2, wherein said GLP-1 agonist is N-$\varepsilon^{26}$-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl][Aib8,Arg34]GLP-1-(7-37)peptide.

16. The solid pharmaceutical composition according to claim 1, wherein said solid pharmaceutical composition comprises
   i) a second coating located between said core and said first coating; and/or
   ii) a further third coating surrounding and containing said core and said first coating.

* * * * *

UNITED STATES PATENT AND TRADEMARK OFFICE
CERTIFICATE OF CORRECTION

PATENT NO. : 10,265,384 B2
APPLICATION NO. : 15/543620
DATED : April 23, 2019
INVENTOR(S) : Birgitte Nissen et al.

It is certified that error appears in the above-identified patent and that said Letters Patent is hereby corrected as shown below:

In the Claims

At Column 64, Claim number 15, Line number 20, please amend as follows:
15. The solid pharmaceutical composition according claim 1, wherein said GLP-1 agonist is N-$\varepsilon^{26}$-[2-(2-[2-(2-[2-(4-(17-carboxyheptadecanoylamino)-4(S)-carboxybutyrylamino]ethoxy)ethoxy]acetylamino)ethoxy]ethoxy)acetyl] [Aib8,Arg34]GLP-1-(7-37)peptide.

Signed and Sealed this
Twenty-fourth Day of December, 2019

Andrei Iancu
*Director of the United States Patent and Trademark Office*